(12) United States Patent
Min

(10) Patent No.: US 8,391,977 B2
(45) Date of Patent: Mar. 5, 2013

(54) MEASUREMENT OF CARDIAC INFORMATION FOR CRT OPTIMZIATION IN THE PRESENCE OF CONDUCTION DYSFUNCTION OR ATRIAL ARRHYTHMIA

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/351,624

(22) Filed: Jan. 17, 2012

(65) Prior Publication Data

US 2012/0116473 A1  May 10, 2012

Related U.S. Application Data

(62) Division of application No. 12/255,544, filed on Oct. 21, 2008, now Pat. No. 8,126,552.

(51) Int. Cl.
*A61N 1/365* (2006.01)
(52) U.S. Cl. .......................................................... 607/17
(58) Field of Classification Search ........................ None
See application file for complete search history.

(56) References Cited

U.S. PATENT DOCUMENTS

| | | |
|---|---|---|
| 4,712,555 A | 12/1987 | Thornander et al. |
| 4,788,980 A | 12/1988 | Mann et al. |
| 4,940,052 A | 7/1990 | Mann et al. |
| 4,944,298 A | 7/1990 | Sholder |
| 5,466,254 A | 11/1995 | Helland |
| 5,476,483 A | 12/1995 | Bornzin et al. |
| 5,690,681 A | 11/1997 | Geddes et al. |
| 5,916,239 A | 6/1999 | Geddes et al. |
| 6,314,323 B1 | 11/2001 | Ekwall |
| 2008/0065166 A1 | 3/2008 | Sathaye et al. |
| 2008/0306567 A1 | 12/2008 | Park et al. |

FOREIGN PATENT DOCUMENTS

WO   9736637   10/1997

OTHER PUBLICATIONS

Restriction Requirement, mailed Sep. 6, 2011—U.S. Appl. No. 12/255,544.
Notice of Allowance, mailed Oct. 24, 2011—U.S. Appl. No. 12/255,544.

*Primary Examiner* — Carl H Layno
*Assistant Examiner* — Paula J Stice

(57) ABSTRACT

An exemplary method includes delivering a cardiac pacing therapy that includes an atrio-ventricular delay and an interventricular delay, providing a paced propagation delay associated with delivery of a stimulus to a ventricle, delivering a stimulus to the ventricle, sensing an event in the other ventricle caused by the stimulus, determining an interventricular conduction delay value based on the delivering and the sensing, determining a interventricular delay ($\Delta_{Sur}$) based on the interventricular conduction delay and the paced propagation delay and determining an atrio-ventricular delay based at least in part on the interventricular delay ($\Delta_{Sur}$). Other exemplary methods, devices, systems, etc., are also disclosed.

11 Claims, 13 Drawing Sheets

DETERMINATION OF $\Delta_{IVCD}$ 600

IVCD_RL 610

RV ———612———

LV ———616———

|←——IVCD_RL——→|

IVCD_LR 620

RV ———626———

|←————IVCD_LR————→|

LV ———622———

$\Delta_{IVCD}$ 630

$\Delta_{IVCD} = IVCD\_LR - IVCD\_RL$

FIG. 6

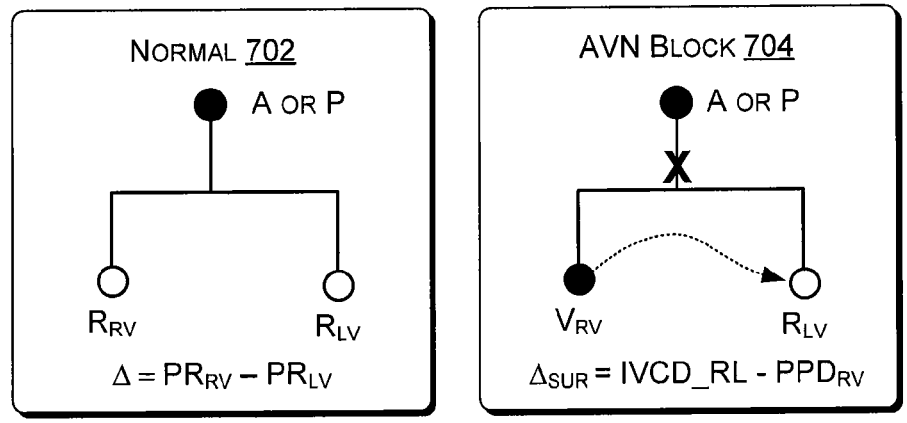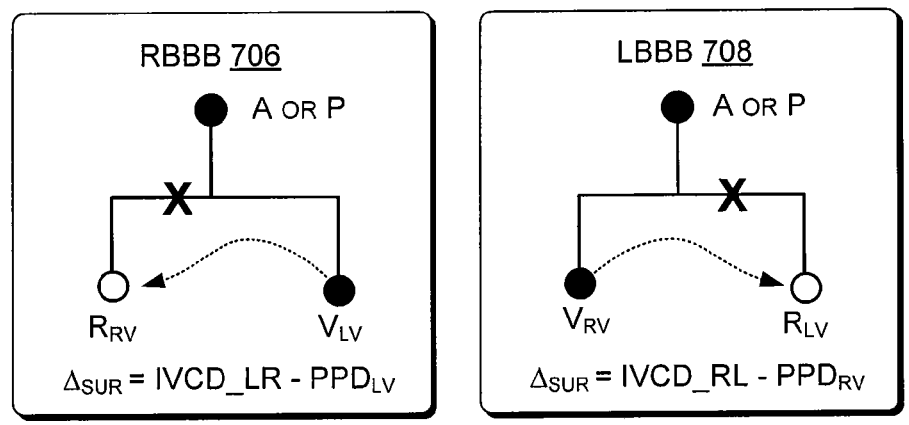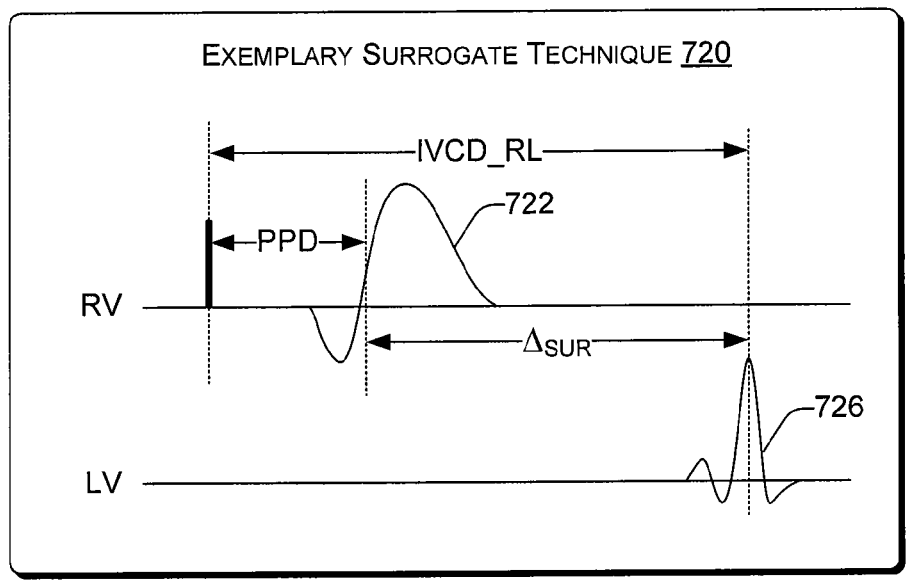
FIG. 7

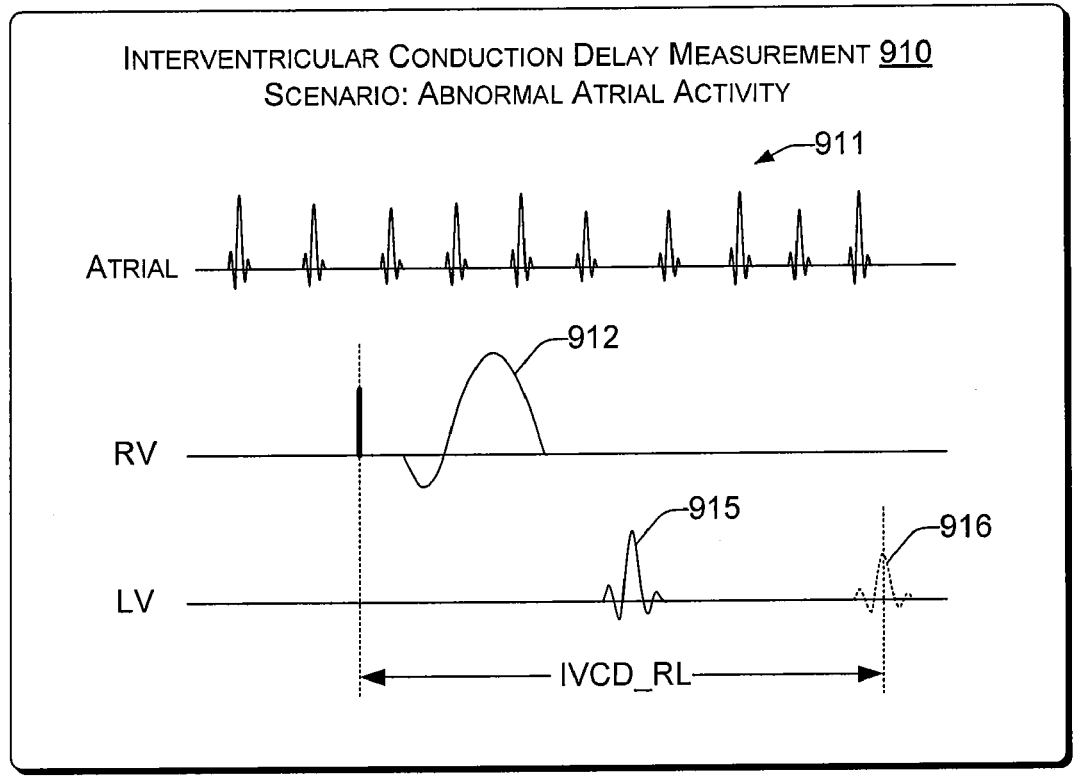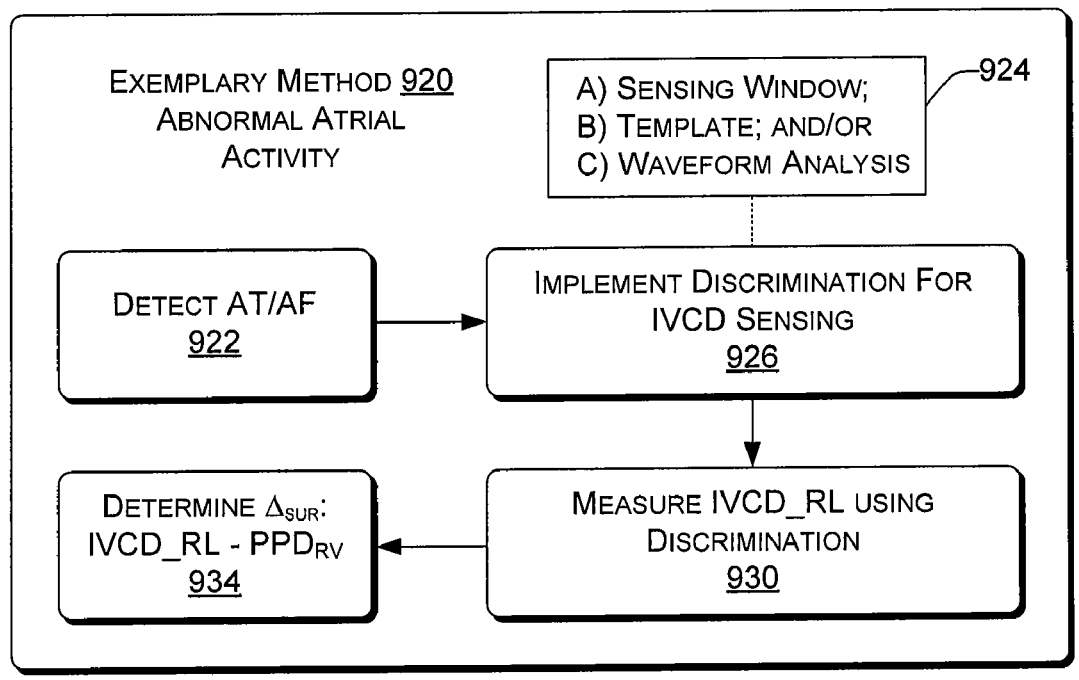
FIG. 9

EXEMPLARY TECHNIQUES 1000
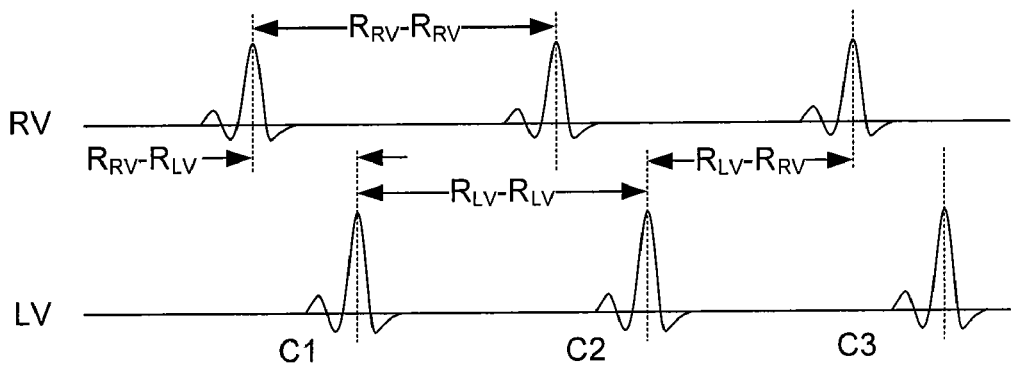
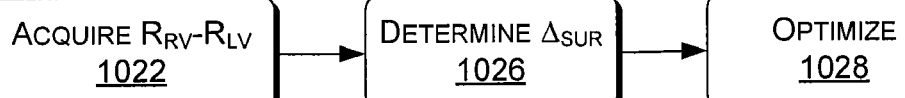
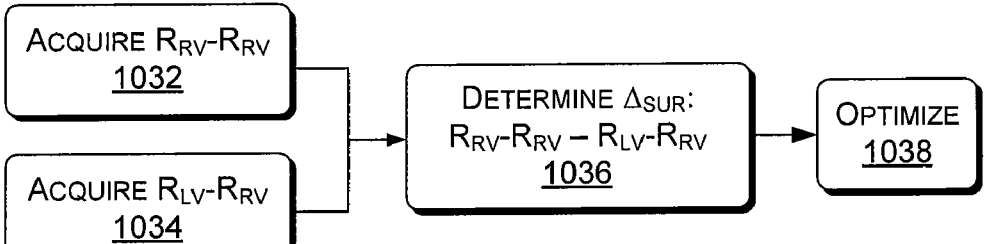
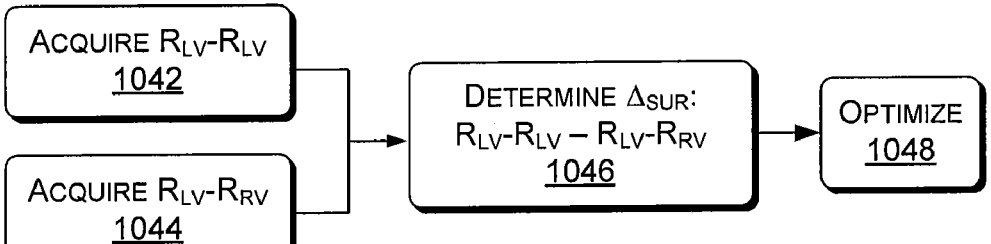
FIG. 10

Exemplary Methods 1200

States 1210

$AS_0$ = Base State (e.g., Rest)
$AS_1$ = Active State 1
$AS_2$ = Active State 2
$AS_N$ = Active State N

PV or AV States 1220

$\beta = \delta/DD(AS_0)$
$\beta = \delta/AD(AS_0)$ $\delta = f(\Delta P(AS_0))$   $\delta = f(\Delta A(AS_0))$
$\delta = f(\Delta P(AS_x))$   $\delta = f(\Delta A(AS_x))$ $PV(AS_0) = \Delta P(AS_0) + \delta$
$AV(AS_0) = \Delta A(AS_0) + \delta$ $PV(AS_x) = \Delta P(AS_x) + \beta*DD(AS_x)$
$AV(AS_x) = \Delta A(AS_x) + \beta*AD(AS_x)$ $PV(AS_0) = \Delta P(AS_0) + \delta - PL$
$AV(AS_0) = \Delta A(AS_0) + \delta - PL$ $PV(AS_x) = \Delta P(AS_x) + \beta*DD(AS_x) - PL$
$AV(AS_x) = \Delta A(AS_x) + \beta*AD(AS_x) - PL$

VV States 1230

$\alpha$ = Constant
$\alpha = \alpha(AS_0)$
$\alpha = \alpha(AS_x)$ $\Delta(AS_0) = R_{LV}(AS_0) - R_{RV}(AS_0)$
$\Delta(AS_x) = R_{LV}(AS_x) - R_{RV}(AS_x)$ $\Delta_{IVCD}(AS_0) = IVCD\text{-}LR(AS_0) - IVCD\text{-}RL(AS_0)$
$\Delta_{IVCD}(AS_x) = IVCD\text{-}LR(AS_x) - IVCD\text{-}RL(AS_x)$ $VV(AS_0) = \alpha*(\Delta(AS_0) + \Delta_{IVCD}(AS_0))$
$VV(AS_x) = \alpha*(\Delta(AS_x) + \Delta_{IVCD}(AS_x))$ $VV(AS_0) = \alpha*(\Delta(AS_0) + \Delta_{IVCD}(AS_0)) - \Delta PL$
$VV(AS_x) = \alpha*(\Delta(AS_x) + \Delta_{IVCD}(AS_x)) - \Delta PL$

FIG. 12

MEASUREMENT OF CARDIAC INFORMATION FOR CRT OPTIMZIATION IN THE PRESENCE OF CONDUCTION DYSFUNCTION OR ATRIAL ARRHYTHMIA

CROSS REFERENCE TO RELATED APPLICATIONS

This application is a division U.S. patent application Ser. No. 12/555,554, U.S. Pat. No. 8,126,552 filed Oct. 21, 2008, titled Measurement of Cardiac Information for CRT Optimization in the Presence of Conduction Dysfunction or Atrial Arrhythmia, and is incorporated by reference herein in its entirety.

TECHNICAL FIELD

Exemplary techniques presented herein generally relate to cardiac therapy. Various exemplary techniques allow for measurement of information germane to cardiac resynchronization therapy in the presence of one or more cardiac conditions.

BACKGROUND

Cardiac resynchronization therapy (CRT) can increase quality of life by improving cardiac performance. Most CRTs rely on a set of parameters that can be optimized according to various criteria. As cardiac conditions change, for better or worse, such parameters may be periodically re-optimized. In general, benefits of CRT increase with frequency of optimization. However, certain cardiac conditions can confound optimization or otherwise make optimization problematic. For example, conditions such as bundle branch block (BBB), atrio-ventricular nodal block (AVN block) and atrial fibrillation (AF) often occur in conjunction with congestive heart failure (CHF) and can confound measurement of some intervals used in the QuickOpt™ optimization algorithm (St. Jude Medical, Inc., Sylmar, Calif.). Consider AVN block due to disease or surgically performed AVN ablation; such a patient is often considered pacing dependent due to the lack of proper conduction from the atria to the ventricles. Thus, the condition of AVN block confounds an optimization algorithm for CRT or other pacing therapy that relies an intrinsic atrio-ventricular interval for the right ventricle (RV) or the left ventricle (LV). Consequently, a need exists for techniques to, for example, measure one or more intervals in the presence of AVN block as well as other cardiac conditions. Various exemplary techniques described herein address this need and/or other needs.

SUMMARY

An exemplary method includes delivering a cardiac pacing therapy that includes an atrio-ventricular delay and an interventricular delay, providing a paced propagation delay associated with delivery of a stimulus to a ventricle, delivering a stimulus to the ventricle, sensing an event in the other ventricle caused by the stimulus, determining an interventricular conduction delay value based on the delivering and the sensing, determining a interventricular delay ($\Delta_{Sur}$) based on the interventricular conduction delay and the paced propagation delay and determining an atrio-ventricular delay based at least in part on the interventricular delay ($\Delta_{Sur}$). Other exemplary methods, devices, systems, etc., are also disclosed.

In general, the various devices, methods, etc., described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

FIG. 6 is a block diagram of an exemplary method for measuring an interventricular conduction delay from the right ventricle to the left ventricle (IVCD_RL) and from the left ventricle to the right ventricle (IVCD_LR).

FIG. 7 is a block diagram of an exemplary method for measuring a surrogate value for the delay $\Delta$.

FIG. 9 is a plot that illustrates how an atrial arrhythmia can confound measurement of an interventricular conduction delay (IVCD) along with a block diagram of an exemplary method to measure an IVCD in the presence of atrial arrhythmia.

FIG. 10 is a plot of right ventricular activity and left ventricular activity and associated intervals along with block diagrams for three exemplary methods that rely, at least in part, on a time of a right ventricular event and a left ventricular event.

FIG. 12 is a series of equations for use in various exemplary methods for single ventricular pacing and/or bi-ventricular pacing therapies.

DETAILED DESCRIPTION

The following description includes the best mode presently contemplated for practicing the described implementations.

This description is not to be taken in a limiting sense, but rather is made merely for the purpose of describing the general principles of the implementations. The scope of the described implementations should be ascertained with reference to the issued claims. In the description that follows, like numerals or reference designators generally reference like parts or elements.

Overview

Various pacing techniques rely on so-called "tests" to acquire information, which, in turn, is used to optimize pacing delivery. Such tests are typically developed to operate under normal conditions. However, under abnormal conditions such as arrhythmia or conduction block, such tests may fail. Under some conditions, a test may be disabled (e.g., a feature turned off) as, under such conditions, the acquired information may be unreliable or otherwise inaccurate. As described herein, various exemplary alternatives exist for reliable measurement of one or more parameter values, referred to herein as a surrogate value or values.

The description that follows discuses an example of an implantable device configured to deliver cardiac pacing therapy, various exemplary methods that include use of a paced propagation delay or intervals to aid in optimization of pacing parameters and an exemplary system configured to implement one or more of the exemplary methods.

Some examples refer to optimization of AV, PV and/or VV. The QuickOpt™ algorithm can determine values for these parameter using so-called "V sense", "RV Pace" and "LV Pace" tests. However, without alternative techniques, heart block patients are excluded from use of "V Sense" tests because of the need to measure atrial conduction to a RV sensing site and to a LV sensing site to calculate a peak to peak conduction delay (e.g., Δ). Yet, other tests, such as "A sense" or "A Pace", "RV Pace" and "LV Pace" can still be implemented for heart block patients.

For AF patients in "auto mode switch (AMS), "V sense" tests become unreliable for the timing relationship of the RV QRS and the LV QRS. Other issues may also exist for patients experiencing abnormal atrial activity.

In general, atrial arrhythmia and conduction problems can confound measurements required for pacing optimization. As described in more detail below, techniques that include measurement of a paced propagation delay and/or intervals can aid in optimizing therapy for patients with such conditions.

Exemplary Stimulation Device

The techniques described below are intended to be implemented in connection with any stimulation device that is configured or configurable to stimulate nerves and/or stimulate and/or shock a patient's heart.

Figure 1:
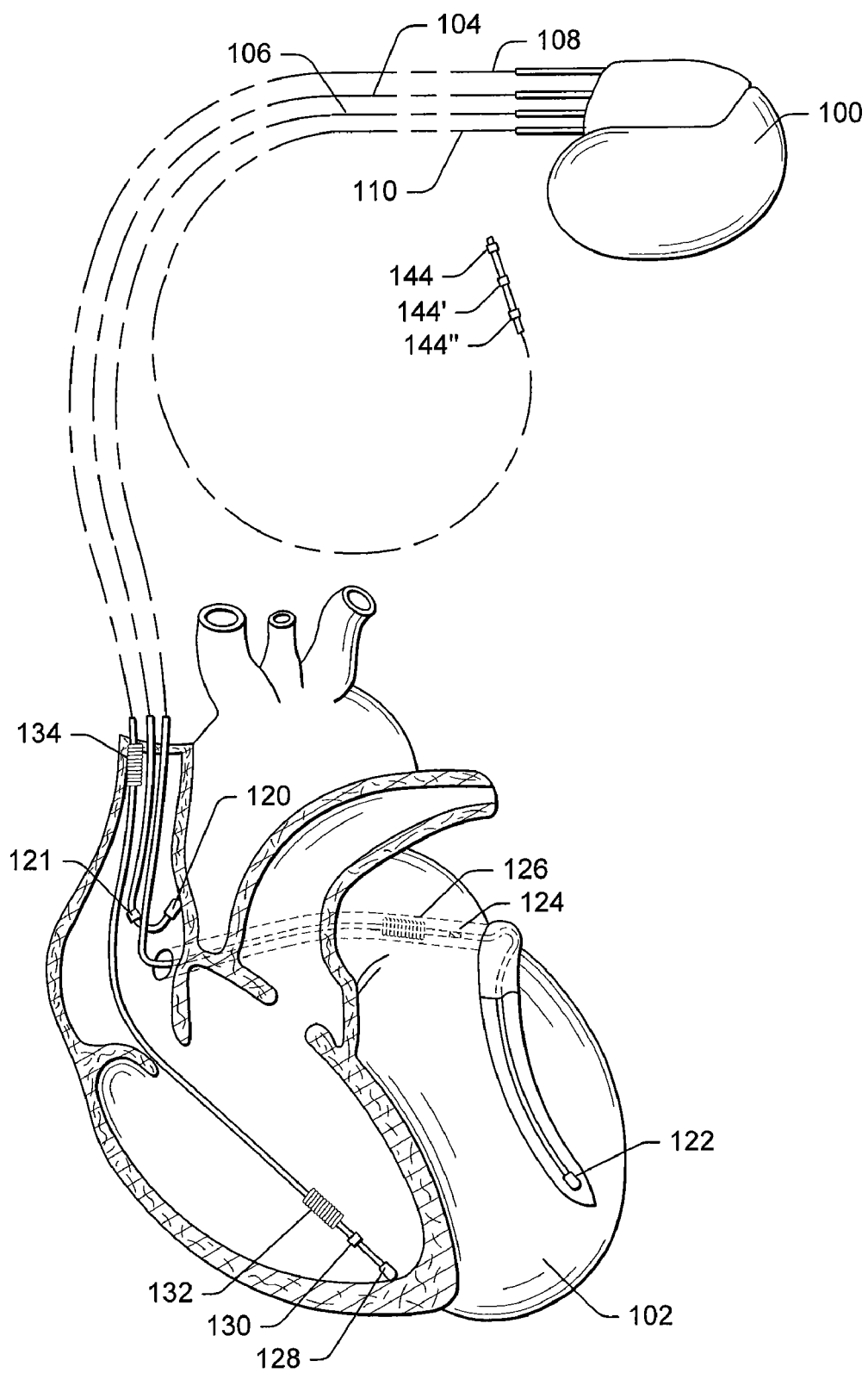
FIG. 1 is a simplified diagram illustrating an exemplary implantable stimulation device in electrical communication with at least three leads implanted into a patient's heart and at least one other lead for delivering stimulation and/or shock therapy. Various exemplary methods may be implemented by an implantable device that includes a different number of leads (e.g., fewer or more than shown in the example of FIG. 1).

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
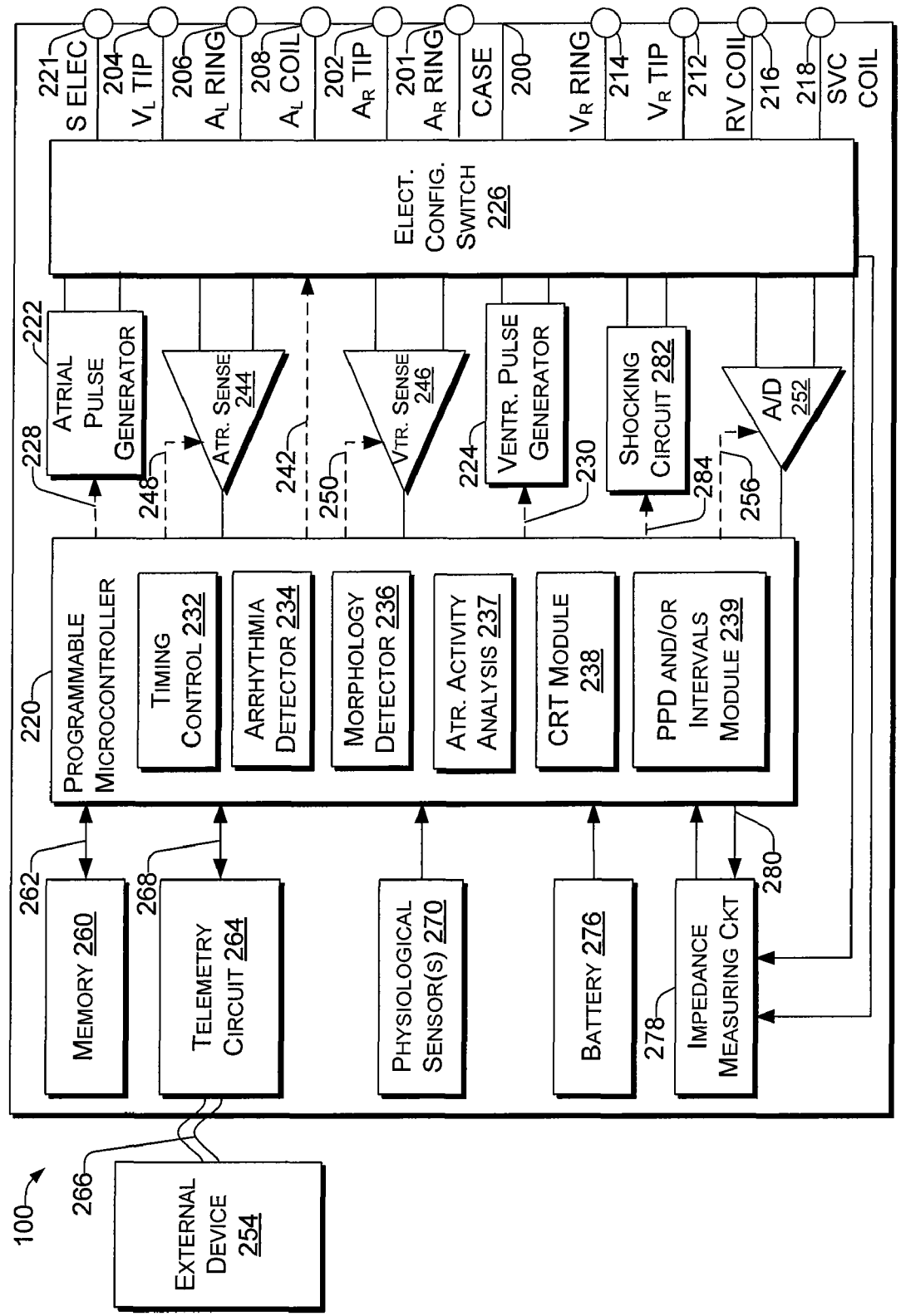
FIG. 2 is a functional block diagram of an exemplary implantable stimulation device illustrating basic elements that are configured to provide cardioversion, defibrillation, pacing stimulation and/or other tissue stimulation (e.g., muscle, nerve, etc. stimulation). The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular delay (AV or more specifically $AV_{RV}$ or $AV_{LV}$), atrial interconduction delay (e.g., A–A or more specifically $A_R$–$A_L$ or $A_L$–$A_R$), or ventricular interconduction delay (VV or more specifically $V_{LV}$–$V_{RV}$ or $V_{RV}$–$V_{LV}$), etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an atrial activity analysis module 237. The atrial activity analysis module 237 optionally implements one or more methods for sensing, information analysis, and/or stimulation control related to atrial activity. For example, the atrial activity analysis module 237 optionally implements one or more of the exemplary methods described below.

Microcontroller 220 further includes a cardiac resynchronization therapy (CRT) module 238 for performing a variety of tasks related to CRT. For example, the CRT module 238 may implement a therapy that relies on pacing a ventricle or pacing both ventricles to promote mechanical synchrony and cardiac performance. The CRT module 238 may be implemented in hardware as part of the microcontroller 220, or as software/firmware instructions programmed into the device and executed on the microcontroller 220 during certain modes of operation. The CRT module 238 may optionally implement various exemplary methods described herein.

As described herein, the microcontroller 220 includes a module 239 for performing a variety of tasks related to paced propagation delays (PPDs) and/or intervals. A paced propagation delay (PPD) may be considered a "travel" time for a wavefront and may be measured from a delivery time of a stimulus to a feature time as sensed on a wavefront resulting from the stimulus (e.g., a feature of an evoked response). For example, a paced propagation delay may be measured from a delivery time of a right ventricular stimulus to a maximum positive slope (e.g., repolarization) of an evoked response in the right ventricle. The module 239 may provide information to the module 238 to help determine one or more parameters for delivery of CRT.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) to determine a type of remedial therapy, if so desired (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
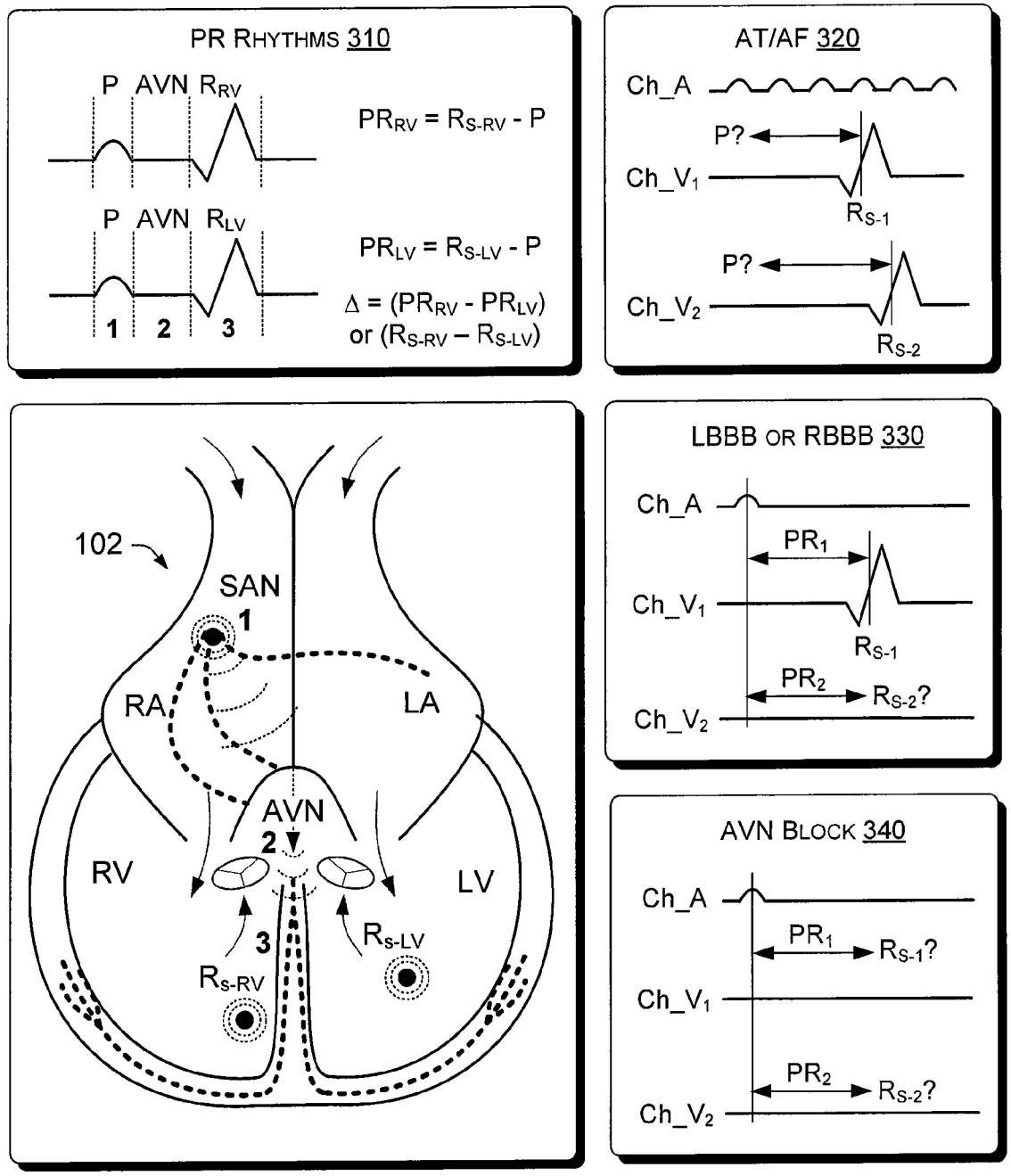
FIG. 3 is a diagram of the heart along with plots of normal heart rhythms, atrial tachycardia/fibrillation, bundle branch block and atrio-ventricular nodal block.

Referring to FIG. 3, an approximate anatomical diagram of a heart 102 is shown along with waveforms for normal PR rhythms 310, atrial tachycardia (AT) and/or atrial fibrillation (AF) 320, left bundle branch block (LBBB) or right bundle branch block (RBBB) 330, and atrio-ventricular node (AVN) block 340.

Referring to the heart 102, action potentials propagating through the heart 102 are labeled as follows: 1, associated with the sinoatrial node (SAN) and the atria; 2, associated with the atrioventricular node (AVN); and 3, associated with right and left bundle branches of the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

While the SAN is mentioned as a source for initiating depolarization of the atria, depolarization is generally initiated from a region in the high right atrium and not particularly at a discrete site (i.e., not solely at a point definable as the SAN). Hence, the SAN is typically not the sole driver but rather a region that extends around the SAN initiates atrial depolarization where the specific region may migrate and result in some degree of rhythm change.

The waveforms for PR rhythms 320 show an atrial event (P) at the SAN 1, propagation of the resulting atrial waveform though the AVN 2 and to the bundle branches of the ventricles 3 where contractions occur ($R_{RV}$, $R_{LV}$). Equations are shown for the RV and LV where $PR_{RV}=R_{S\text{-}RV}-P$ and $PR_{LV}=R_{S\text{-}LV}-P$. In the example of FIG. 3, a parameter Δ can be calculated as $PR_{RV}-PR_{LV}$ or alternatively $R_{S\text{-}RV}-R_{S\text{-}LV}$. This parameter represents the time difference between contraction of the RV and LV; hence, the parameter Δ indicates degree of synchrony or lack thereof (i.e., dyssynchrony). For example, if one patient has a value for Δ of 10 ms and another patient has a value for Δ of 100 ms, the latter patient has significant dyssynchrony compared to the former. Various algorithms rely on knowledge of synchrony or dyssynchrony. However, as explained with respect to the waveforms 320, 330 and 340, certain cardiac conditions can make measurement of synchrony/dyssynchrony problematic.

For the AT/AF condition 320, intrinsic atrial rate, if definable, becomes quite high. In such a circumstance, conduction of atrial activity through the AVN may occur sporadically where one of the many waveforms causes depolarization of the RV and the LV. As $PR_{RV}$ and $PR_{LV}$ rely on knowing the time of a P wave, the intervals $PR_{S-1}$ and $PR_{S-2}$ cannot be readily determined (where 1 represents the right or left ventricle and where 2 represents the left or right ventricle). As an alternative, if timing of both $R_{S-1}$ and $R_{S-2}$ can be measured for a single cardiac cycle, then these timings may be used to determine $\Delta$. As described below, various exemplary techniques can be used to determine a surrogate value for the parameter $\Delta$ where AT/AF exists.

For the LBBB or RBBB condition 330, time of an atrial event may be known as well as the time of an associated ventricular event, however, for the other ventricle, BBB prevents the atrial event from directly causing an associated ventricular event for that ventricle. Thus, PR may be known for one ventricle and not for the other. While the PR time for the ventricle with bundle branch conduction together with time of an event in the other ventricle, the time of the event in the other ventricle may not be an accurate representation of the parameter $\Delta$ as such a time would include, for example, the time it takes for a depolarization wavefront from the ventricle with conduction to travel to the ventricle with BBB. Hence, as described below, various exemplary techniques can be used to determine a surrogate value for the parameter $\Delta$. where LBBB or RBBB exists.

For the AVN block condition 340, atrial events do not conduct via the AVN to the ventricles in any reliable manner. Consequently, a patient having such a condition is pacing dependent and measurement of PV or AV for either ventricle is not possible. As described below, various exemplary techniques can be used to determine a surrogate value for the parameter $\Delta$ where AVN block exists.

Figure 4:
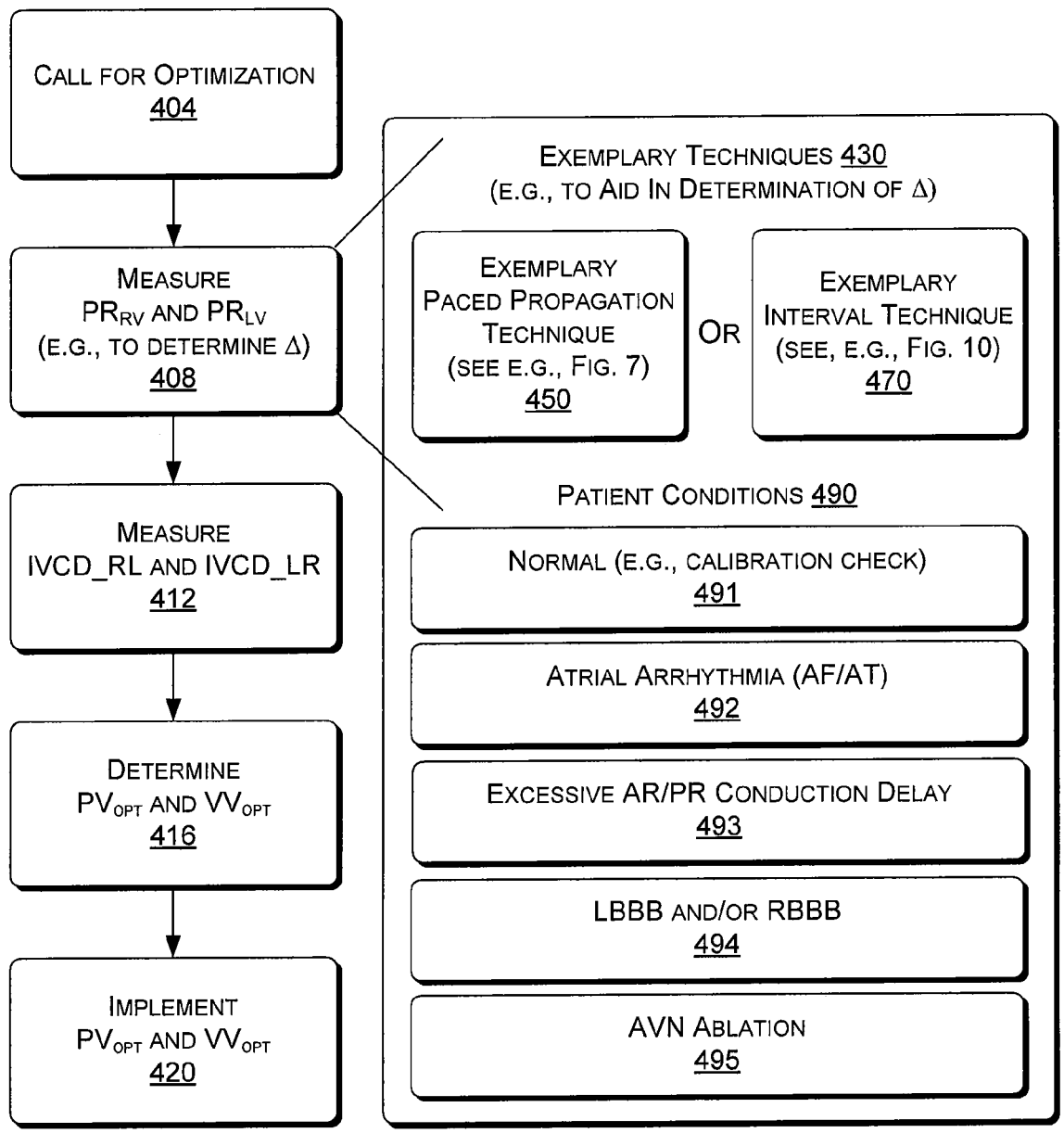
FIG. 4 is a block diagram of an exemplary method for optimizing one or more pacing parameters along with exemplary techniques to aid in determining an intrinsic delay $\Delta$ (e.g., $PR_{LV}-PR_{RV}$).

FIG. 4 shows an exemplary method 400 for optimizing cardiac therapy. As described herein, various exemplary techniques 430 can aid in determination of a parameter $\Delta$ (e.g., a surrogate $\Delta$, $\Delta_{Sur}$). The method 400 is described first followed by a description of the techniques 430.

The method 400 may be used to determine one or more parameters, such as PV, AV, VV, etc., for optimizing delivery of cardiac therapy. The method 400 commences in a call block 404 that calls for optimization of cardiac therapy. A measurement block 408 follows that measures $PR_{RV}$ and $PR_{LV}$ intervals, noting that for atrial pacing, $AR_{RV}$ or $AR_{LV}$ may be substituted. The technique to measure PR or AR is sometimes referred to as a "V sense" test. Hence to determine a value for the parameter $\Delta$, an implantable device typically performs a right ventricular V sense test to acquire a right ventricular PR or AR time and a left ventricular V sense test to acquire a left ventricular PR or AR time where $\Delta$ is equal to the time difference between the two times.

Another measurement block 412 measures interventricular conduction delays (IVCDs) in a direction from the right ventricle to the left ventricle (IVCD_RL) and in a direction from the left ventricle to the right ventricle (IVCD_LR). In general, a stimulus is delivered to one ventricle and a conducted wavefront is sensed in the other ventricle (see, e.g., FIG. 6). Such an IVCD may be referred to as a paced IVCD. Alternatively, a sensed IVCD may be used where an intrinsic event is sensed in one ventricle and a conducted wavefront associated with the sensed intrinsic event is sensed in the other ventricle. In either instance, the IVCD provides information about directional conduction between the ventricles. Such information, as explained below, can be used to optimize one or more cardiac therapy parameters.

Given the measurements of blocks 408 and 412, the method 400 continues in a determination block 416 that determines an optimal PV interval ($PV_{Opt}$) and an optimal VV interval ($VV_{Opt}$). Alternatively, or in addition to, an optimal AV interval ($AV_{Opt}$) may be determined, where appropriate. After the determination block 416, an implementation block 420 implements a cardiac therapy using at least one of the one or more parameters.

An exemplary method may determine $VV_{Opt}$ using the following equation: $VV_{Opt} = \alpha(\Delta + \Delta_{IVCD})$, where $\Delta = R_{LV} - R_{RV}$, $\Delta_{IVCD} = IVCD\_LR - IVCD\_RL$ and $\alpha$ may be approximately 0.5 (or other suitable value). For this equation, if $VV_{Opt}$ is greater than 0, then the left ventricle is paced first (i.e., prior to the right ventricle) and if $VV_{Opt}$ is less than 0, then the right ventricle is paced first (i.e., prior to the left ventricle). Consider an example where $\Delta = 60$ ms and $\Delta_{IVCD}$ is $-4$ ms, then for $\alpha = 0.5$, $VV_{Opt}$ is 28 ms. A biventricular pacing therapy would then pace the left ventricle 28 ms prior to pacing the right ventricle.

With respect to parameters used in optimization or delivery of a cardiac therapy, such parameters may include:

PP, AA Interval between successive atrial events

PV Delay between an atrial event and a paced ventricular event $PV_{optimal}$ Optimal PV delay $PV_{RV}$ PV delay for right ventricle $PV_{LV}$ PV delay for left ventricle AV Delay for a paced atrial event and a paced ventricular event $AV_{optimal}$ Optimal AV delay $AV_{RV}$ AV delay for right ventricle $AV_{LV}$ AV delay for left ventricle $\Delta$ Estimated interventricular delay (e.g., $AV_{LV} - AV_{RV}$)

$\Delta_{programmed}$ Programmed interventricular delay (e.g., a programmed VV delay)

$\Delta_{optimal}$ Optimal interventricular delay

IVCD_RL Delay between an RV event and a consequent sensed LV event

IVCD_LR Delay between an LV event and a consequent sensed RV event $\Delta_{IVCD}$ Difference between interventricular conduction delays (e.g., IVCD_LR–IVCD_RL)

$\Delta P$, $\Delta A$ Width of an atrial event

As described herein, one or more of the measurements of the measurement block 408 may not be possible or lack accuracy. Alternatively, it may be desirable to provide a benchmark to check the accuracy of a $\Delta$ value based on $PR_{RV}$ and $PR_{LV}$ (or $AR_{RV}$ and $AR_{LV}$/or a combination of AR and PR). In such situations, one or more of the exemplary techniques 430 may be used.

The techniques 430 include a paced propagation delay (PPD) based technique 450 and an interval technique 470 (see, e.g., the module 239 of FIG. 2). An exemplary method 700 of FIG. 7 explains a PPD technique while an exemplary method 1000 of FIG. 10 explains an interval technique. With respect to the PPD technique 450, and determining a surrogate for the parameter $\Delta$, consider an RV lead positioned at the endocardial apex. As described herein, use of this lead in conjunction with an LV sensing lead, the technique 450 can provide a surrogate value for the parameter $\Delta$ according to the equation IVCD_RL–$PPD_{RV}$. Similarly, such a technique may be used for the left ventricle (IVCD_LR–$PPD_{LV}$). In some instances, a RV $\Delta_{Sur}$ and a LV $\Delta_{Sur}$ may be determined and one or both (e.g., an average) may be used in place of a V sense based Δ value. In practice, the RV variation may be preferred, especially for patients with conditions such as left bundle branch block (LBBB), which is a found in some HF patients.

FIG. 4 also shows various patient conditions 490 that may prompt use of the technique 450 and/or the technique 470. For example, upon detection of a condition, an exemplary method may call for implementation of the pacing latency technique 450 and/or the interval technique 470. In the example of FIG. 4, the patient conditions include normal condition 491, atrial arrhythmia (e.g., AT or AF) 492, excessive AR/PR conduction delay 493 (e.g., for one or both ventricles), bundle branch block (e.g., LBBB or RBBB) 494 and AVN ablation 495. The latter three conditions 493, 494 and 495 pertain to conditions that affect conduction of depolarization wavefronts from the atria to one or both ventricles.

With respect to normal condition 491, the techniques 430 and/or 470 may, for example, be used to assess a Δ value based on a PR or AR (e.g., compare Δ with $\Delta_{Sur}$). With respect to atrial arrhythmia 492, measurement of PR becomes problematic as does measurement of a corresponding R following an atrial stimulus as it can be difficult to identify which atrial event caused the intrinsic ventricular contraction. Depending on configuration, an implantable device may disable atrial tracking in the presence of atrial arrhythmias such as AT and/or AF. In such situations, the technique 450 and/or the technique 470 may be used in optimizing one or more therapy parameters (e.g., AV, PV, VV) as the techniques 450, 470 can operate without knowledge of atrial event timing.

With respect to excessive AR/PR conduction delay, conduction issues whether congenital, surgical or disease related may prolong AR or PR for the RV and/or LV. Depending on configuration, an implantable device may avoid V sense tests for one or both ventricles if AR or PR exceeds a certain limit (e.g., about 300 ms). In such situations, the technique 450 and/or the technique 470 may be used in optimizing one or more therapy parameters (e.g., AV, PV and/or VV) as the techniques 450, 470 can still operate given an excessive AV/PV conduction delay for the RV and/or LV. As explained with respect to FIG. 7, the pacing latency technique 450 can rely on a so-called "RV pace" test or "LV pace" test where a stimulus is delivered to one ventricle and a corresponding event sensed in the other ventricle. As explained with respect to FIG. 6, V sense tests are used to determine the time between the delivery of the stimulus and the sensed event is a directional interventricular conduction delay (e.g., IVCD_RL or IVCD_LR).

The techniques 450 and/or 470 may be used where a patient suffers from more profound conduction issues such as LBBB and/or RBBB 494 in optimizing one or more therapy parameters (e.g., AV, PV and/or VV). Further, after AVN ablation, the techniques 450 and/or 470 may be used to optimize one or more therapy parameters (e.g., AV, PV and/or W).

Figure 5:
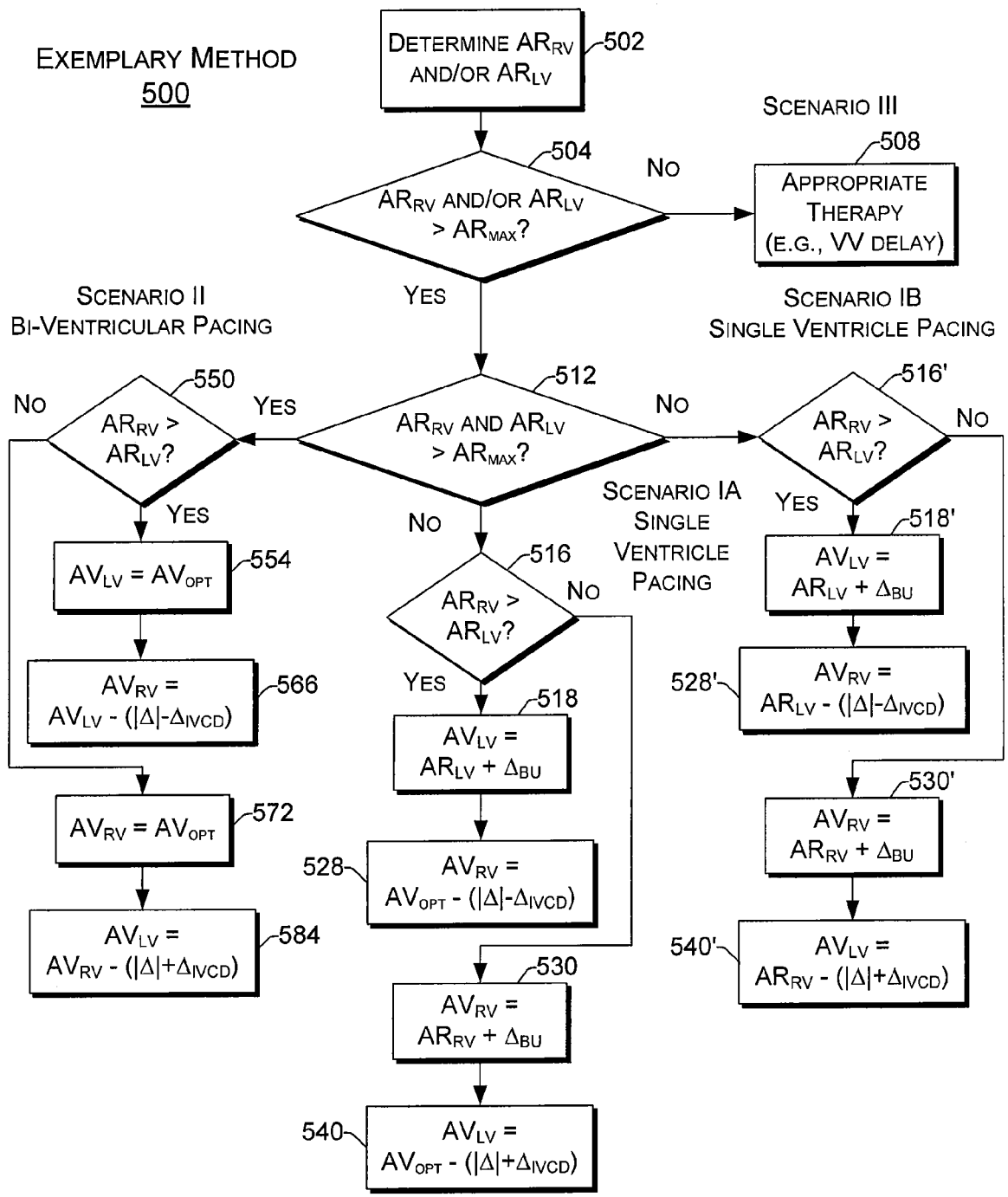
FIG. 5 is a block diagram of an exemplary method for optimizing one or more pacing parameters for single ventricle pacing therapies and/or bi-ventricular pacing therapies.

FIG. 5 shows an exemplary method 500 that includes various algorithms for determining one or more parameters for single and bi-ventricular cardiac pacing therapies. In general, the method 500 expands on the optimization method 400 of FIG. 4. Thus, where the term Δ appears, the techniques 450 and/or 470 may be implemented to determine a surrogate value, $\Delta_{Sur}$. In instances where a patient suffers from a condition such as atrial arrhythmia, certain steps of the method 400 may be performed after the arrhythmia ceases (e.g., on its own or in response to an anti-arrhythmia therapy); whereas, in steps where the term Δ appears in a scenario (e.g., Scenario IA, IB and II), the techniques 450 and/or 470 may be implemented during an atrial arrhythmia to determine a surrogate value, $\Delta_{Sur}$.

In instances where conduction is excessive or blocked, decisions taken by one or more of the various decision blocks (e.g., 504, 512, 516', 516, 550) may be accounted for by a clinician. For example, a clinician may rely on a diagnostic test (e.g., ECG, echocardiogram, etc.) to decide whether Scenario IA, IB, II or III should be implemented for a particular patient and to decide whether the RV or LV should be paced first. In the method 500, Scenarios IA and IB pertain to single ventricle pacing where $\Delta_{Sur}$ can replace Δ in blocks 528, 528', 540 and 540'. In general, for blocks 528 and 540 of Scenario IA, an optimal AV value is known ($AV_{Opt}$) whereas for blocks 528' and 540' of Scenario IB, a value for $AR_{LV}$ or $AR_{RV}$ is known. For the former, a diagnostic test may provide $AV_{Opt}$ whereas, for the latter, $AR_{LV}$ or $AR_{RV}$ may be measured and used if suitable AR conduction exists to the LV or RV, respectively.

While the method 500 refers to atrial pacing, such algorithms may be implemented for therapies that rely on intrinsic atrial activity (e.g., by substituting PV for AV and PR for AR in various blocks). Further, the method 400 may rely on a combination of PV and AV values and a combination of PR and AR values.

As mentioned, the method 500 includes the following scenarios: IA (single ventricle pacing given $AV_{Opt}$); IB (single ventricle pacing given $AR_{LV}$ or $AR_{RV}$); II (bi-ventricular pacing); and III (other appropriate therapy). According to the method 500, a determination block 502 determines $AR_{RV}$ and/or $AR_{LV}$. In a decision block 504 a decision is made as to whether $AR_{RV}$ and/or $AR_{LV}$ have exceeded a predetermined $AR_{max}$ value. If neither value exceeds $AR_{max}$, then Scenario III follows, which may disable ventricular pacing or take other appropriate therapy per block 508. Other appropriate therapy optionally includes therapy that achieves a desirable VV delay by any of a variety of techniques. If however one or both values exceed $AR_{max}$, then the method 500 continues in another decision block 512. The decision block 512 decides whether $AR_{RV}$ and $AR_{LV}$ have exceeded $AR_{max}$. If both values do not exceed $AR_{max}$, then single ventricular pacing occurs, for example, per Scenario IA or Scenario IB. If both values exceed $AR_{max}$, then bi-ventricular pacing occurs, for example, Scenario II.

Scenario IA commences with a decision block 516 that decides if $AR_{RV}$ is greater than $AR_{RV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IA, the method 500 continues in a back-up pacing block 518 where $AV_{LV}$ is set to $AR_{LV}$ plus some back-up time (e.g., $\Delta_{BU}$). The block 518, while optional, acts to ensure that pacing will occur in the left ventricle if no activity occurs within some given interval. The method 500 then continues in a set block 528 where the parameter $\Delta_{IVCD}$ is used as a correction factor to set the $AV_{RV}$ delay to $AV_{optimal}(|\Delta|-\Delta_{IVCD})$.

For left ventricular pacing per the Scenario IA, the method 500 continues in a back-up pacing block 530 where $AV_{LV}$ is set to $AR_{LV}$ plus some back-up time (e.g., $\Delta_{BU}$). The block 530, while optional, acts to ensure that pacing will occur in the left ventricle if no activity occurs within some given interval. The method 500 then continues in a set block 540 where the parameter $\Delta_{IVCD}$ is used as a correction factor to set the $AV_{LV}$ delay to $AV_{optimal}-(|\Delta|+\Delta_{IVCD}$. The parameter $\Delta_{IVCD}$ is calculated as the difference between IVCD_LR and IVCD_RL (e.g., IVCD_LR–IVCD_RL).

Scenario IB commences with a decision block 516' that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing per Scenario IB, the method 500 continues in a back-up pacing block 518' where $AV_{LV}$ is set to $AR_{LV}$ plus some back-up time (e.g., $\Delta_{BU}$). The block 518', while optional, acts to ensure that pacing will occur in the left ventricle if no activity occurs within some given interval. The method 500 then continues in a set block 528' where the parameter $\Delta_{IVCD}$ is used as a correction factor to set the $AV_{RV}$ delay to $AR_{LV}-(|\Delta|-\Delta_{IVCD})$. Hence, in this example, a pre-determined $AV_{optimal}$ is not necessary.

For left ventricular pacing per the Scenario IB, the method 500 continues in a back-up pacing block 530' where $AV_{LV}$ is set to $AR_{LV}$ plus some back-up time (e.g., $\Delta_{BU}$). The block 530', while optional, acts to ensure that pacing will occur in the left ventricle if no activity occurs within some given interval. The method 500 then continues in a set block 540' where the parameter $\Delta_{IVCD}$ is used as a correction factor to set the $AV_{LV}$ delay to $AR_{RV}-(|\Delta|+\Delta_{IVCD})$. Again, in this example, a pre-determined $AV_{optimal}$ is not necessary.

Referring again to the decision block 512, if this block decides that bi-ventricular pacing is appropriate, for example, Scenario II, then the method 500 continues in a decision block 550, which that decides if $AR_{RV}$ is greater than $AR_{LV}$. If $AR_{RV}$ exceeds $AR_{LV}$, then bi-ventricular pacing occurs wherein the right ventricle is the master (e.g., paced prior to the left ventricle or sometimes referred to as left ventricle slave). If $AR_{RV}$ does not exceed $AR_{LV}$, then bi-ventricular pacing occurs wherein the left ventricle is the master (e.g., paced prior to the right ventricle or sometimes referred to as right ventricle slave).

For right ventricular master pacing, the method 500 continues in a set block 554 which sets $AV_{LV}$ to $AV_{optimal}$. The method 500 then uses $\Delta_{IVCD}$ as a correction factor in a set block 566, which sets $AV_{RV}$ delay to $AV_{LV}-(|\Delta|+\Delta_{IVCD})$.

For left ventricular master pacing, the method 500 continues in a set block 572 which sets $AV_{RV}$ to $AV_{optimal}$. The method 500 then uses $\Delta_{IVCD}$ as a correction factor in a set block 584, which sets $AV_{LV}$ delay to $AV_{RV}-(|\Delta|_{IVCD})$.

A comparison between $\Delta$ and $\Delta_{programmed}$ or $\Delta_{optimal}$ can indicate a difference between a current cardiac therapy or state and a potentially better cardiac therapy or state. For example, consider the following equation:

$$\alpha = \Delta_{optimal}/\Delta$$

where $\alpha$ is an optimization parameter. Various echocardiogram studies indicate that the parameter $\alpha$ is typically about 0.5. The use of such an optimization parameter is optional. The parameter $\alpha$ may be used as follows:

$$AV_{RV}=AV_{optimal}-\alpha|\Delta| \text{ or } PV_{RV}=PV_{optimal}-\alpha|\Delta|$$

$$AV_{LV}=AV_{optimal}-\alpha(|\Delta|+\Delta_{IVCD}) \text{ or}$$

$$PV_{LV}=PV_{optimal}-\alpha(|\Delta|+\Delta_{IVCD})$$

If a parameter such as the aforementioned a parameter is available, then such a parameter is optionally used to further adjust and/or set one or more delays, as appropriate.

Various exemplary methods, devices, systems, etc., may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equation may be used in such a situation:

$$AV_{LV}=AR_{RV}-|\Delta| \text{ or } PV_{LV}=PR_{RV}-|\Delta|$$

This equation is similar to the equation used in blocks 528' and 540' of Scenario IB of FIG. 5. With respect to backup pulses, a backup pulse (e.g., for purposes of safety, etc.) may be set according to the following equation:

$$AV_{RV}=AR_{RV}+|\gamma| \text{ or } PV_{RV}=PR_{RV}+|\gamma|$$

Of course, administration of a backup pulse may occur upon one or more conditions, for example, failure to detect activity in the particular ventricle within a given period of time. In the foregoing equation, the parameter $\gamma$ is a short time delay, for example, of approximately 5 ms to approximately 10 ms. This equation is similar to the equation used in blocks 518' and 530' of Scenario IB of FIG. 5.

In many instances, heart condition will affect $AR_{RV}$ and $AR_{LV}$, and IVCD (e.g., IVCD_RL and/or IVCD_LR), which, in turn, may affect an existing optimal VV delay setting. As explained with respect to the method 400 of FIG. 4, an algorithm may update an existing optimal VV delay. A trigger may initiate an update according to a predetermined time or event period or activity sensors for exercise, resting, etc. An exemplary device may include a learning method that learns based on differences in conduction times (e.g., $AR_{RV}$ and $AR_{RV}$, IVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional. Further, use of internal measurement or sensing equipment for sensing pressure or other indicators of hemodynamic performance is optional. Again, adjustment and learning may rely on IEGM information and/or cardiac other rhythm information.

The method 400 and the method 500 include use of IVCD_RL and IVCD_LR. Measurement of IVCD_RL or IVCD_LR is usually accomplished by simply delivering a stimulus to one ventricle and sensing related activity in the other ventricle. However, situations exist that can make such measurements difficult.

FIG. 6 shows a method 600 for determining a value for the parameter $\Delta_{IVCD}$. In the example of FIG. 6, the method 600 commences in a measurement block 610 to measure IVCD_RL. At an initial time, $T_0$, a stimulus is delivered to the RV and an evoked response generated 612. The evoked response conducts to the LV where corresponding electrical activity 616 is sensed at a time $T_{LV}$. Given $T_0$ and $T_{LV}$, the time difference between $T_0$ and $T_{LV}$ (e.g., $T_{LV}-T_0$) determines the value of IVCD_RL. A measurement block 620 follows to measure IVCD_LR. At an initial time, $T_0$, a stimulus is delivered to the LV and an evoked response generated 612. The evoked response conducts to the RV where corresponding electrical activity 626 is sensed at a time $T_{RV}$. Given $T_0$ and $T_{RV}$, the time difference between $T_0$ and $T_{RV}$ (e.g., $T_{RV}-T_0$) determines the value of IVCD_LR. Given values for IVCD_RL and IVCD_LR, a value for $\Delta_{IVCD}$ can be calculated as IVCD_LR-IVCD_RL, according to the convention discussed with respect to FIG. 5. In the method 600, the order of blocks 610 and 620 may be reversed.

In general, the time between delivery of a stimulus in one ventricle (or a feature of an evoked response) and the corresponding sensed event in the other ventricle is representative of conduction between the delivery location of the stimulus for one ventricle and the sensing location of the corresponding event for the other ventricle. The method 600 may be valid for the following scenarios (i) no atrio-ventricular conduction exists, (ii) atrio-ventricular conduction exists for a single ventricle, and (iii) atrio-ventricular conduction exists for both ventricles.

For scenario (iii), the conduction time IVCD_LR may be less than $PR_{RV}-PV_{LV}$; hence, where the left ventricular stimulus is delivered at a time $PV_{LV}$, any atrial event (intrinsic event P) will not conduct to the right ventricle and generate an R wave ($R_{RV}$) before sensing of the sensed event 626 occurs. In contrast, if IVCD_LR is greater than $PR_{RV}-PV_{LV}$, then conduction of the left ventricular stimulus and evoked response 622 to the right ventricular sensing location (event 626) can occur after a right ventricular R wave caused by intrinsic atrial activity. Thus, measurement of IVCD_LR may be problematic; noting that a similar situation exists for measurement of IVCD_RL. Further, for scenario (ii), similar situations may confound measurement of IVCD_RL or IVCD_LR.

As described herein, various techniques exist to overcome the aforementioned issues. For example, a discrimination technique can distinguish an event in one ventricle caused by atrio-ventricular conduction of an atrial event from an event in that ventricle caused by an evoked response in the other ventricle. Some discrimination techniques include A) a sensing window; B) a template; and C) waveform analysis. A sensing window may commence sensing activity in the right ventricle after a time $PR_{RV}$, given that $PR_{RV}$ is less than $PV_{LV}+$"IVCD_LR". Further, a shortened PV (e.g., for $PV_{LV}$) may be set to in the case that $PR_{RV}$ is about the same as $PV_{LV}+$IVCD_LR.

FIG. 7 shows various exemplary scenarios 700 that can apply an exemplary technique 720 for determining a surrogate value for the parameter Δ. The technique 720 may be applied in a normal situation 702, where AVN block exists 704, where RBBB exists 706 and where LBBB exists 708. Further, as explained with respect to FIG. 4, the technique 720 may be applied where atrio-ventricular conduction to a ventricle is excessive (e.g., compared to some conduction limit).

The technique 720 is similar to the techniques 610 and 620 of the method 600 of FIG. 6, however, the technique 720 is for measurement of a surrogate value for the parameter Δ (i.e., $\Delta_{Sur}$) and it can rely on a paced propagation delay (PPD). In FIG. 7, the paced propagation delay is the time from delivery of a stimulus in a ventricle to the time of an evoked response 722 in that ventricle, where the time of an evoked response may be determined in any of a variety of manners. For example, the time of the evoked response may be based on an amplitude peak, a maximum slope, a baseline crossing, a deviation from a baseline value, etc. As mentioned with respect to the module 239 of FIG. 2, the paced propagation delay may be viewed as a travel time for a propagating wavefront that originates at an electrode (or electrodes). A particular technique relies on an evoked response time based on a repolarization slope of myocardium immediately after depolarization; noting that the sensing arrangement may present this slope in a positive or negative direction (examples shown in a positive direction). Specifically, as described herein, $\Delta_{Sur}$ is equal to IVCD_RL−$PPD_{RV}$ or IVCD_LR−$PPD_{LV}$. Given these equations, the surrogate value ($\Delta_{Sur}$) may be viewed as being based on two travel times: a total travel time (e.g., from point A to point C) and a travel time for a segment of the "journey" (e.g., from point A to point B, where point B may be considered as being intermediate points A and C).

For the normal conduction scenario 702, the technique 720 may be used as an alternative or in addition to the conventional technique for determining Δ. For the AVN block scenario 704, the technique 720 replaces the conventional technique as the lack of atrio-ventricular conduction prevents measurement of PR or AR for both ventricles. For the RBBB scenario 706, the technique 720 replaces the conventional technique as the lack of atrio-ventricular conduction to the RV prevents measurement of $PR_{RV}$ or $AR_{RV}$. For the LBBB scenario 708, the technique 720 replaces the conventional technique as the lack of atrio-ventricular conduction to the LV prevents measurement of $PR_{LV}$ or $AR_{LV}$.

With respect to the technique 720, consider an RV stimulation site at, or proximate to, the interventricular septum, which is a conduction path from the atria to the ventricles. If a stimulus is delivered at this site, to some extent it mimics a conducted atrial event. However, with respect to timing, to mimic the timing of an intrinsic event more closely the time of delivery of the stimulus is adjusted; alternatively, a time of the evoked response associated with the stimulus may be used. Hence, the exemplary technique 720 defines a surrogate value for the parameter Δ (e.g., $\Delta_{Sur}$) as IVCD_RL−$PPD_{RV}$, or, alternatively, a surrogate value for the parameter Δ (e.g., $\Delta_{Sur}$) may be defined as a time of an evoked response (e.g., 722) in one ventricle to a corresponding event in the other ventricle (e.g., 726). While interventricular septum is given as a possible site, other sites for RV stimulation include RV apex and outflow tract. Such sites are proximate to the main conduction pathway from the atria to the ventricles.

Referring to FIG. 1, using the leads 106 and 108, a stimulation site at or proximate to an atrio-ventricular conduction path (e.g., bundle of His, a site positioned prior to distinct branching of LBB and RBB, etc.) is, conventionally, more readily achievable for the RV than for the LV (e.g., compare position of electrode 128 to position of electrode 122. Hence, the technique 720 may preferably rely on delivery of a stimulus in the RV and sensing in the LV.

In another exemplary technique, where AVN block exists (see scenario 704 of FIG. 7), when determining an interventricular delay (VV), the term Δ may be set to zero and the correction term $\Delta_{IVCD}$ used. In such an approach, the parameter α may be set to unity, for example, instead of one-half (0.5). Further, where the term $\Delta_{IVCD}$ is relied on and not Δ, a device may forego performing measurements for determination of Δ. (e.g., when AVN block is detected or indicated, then prohibit certain measurements). Hence, where AVN blocks exists, then one or more of the various exemplary methods described herein may be used (e.g., $\Delta_{Sur}$, Δ=0 and/or interval techniques).

Figure 8:
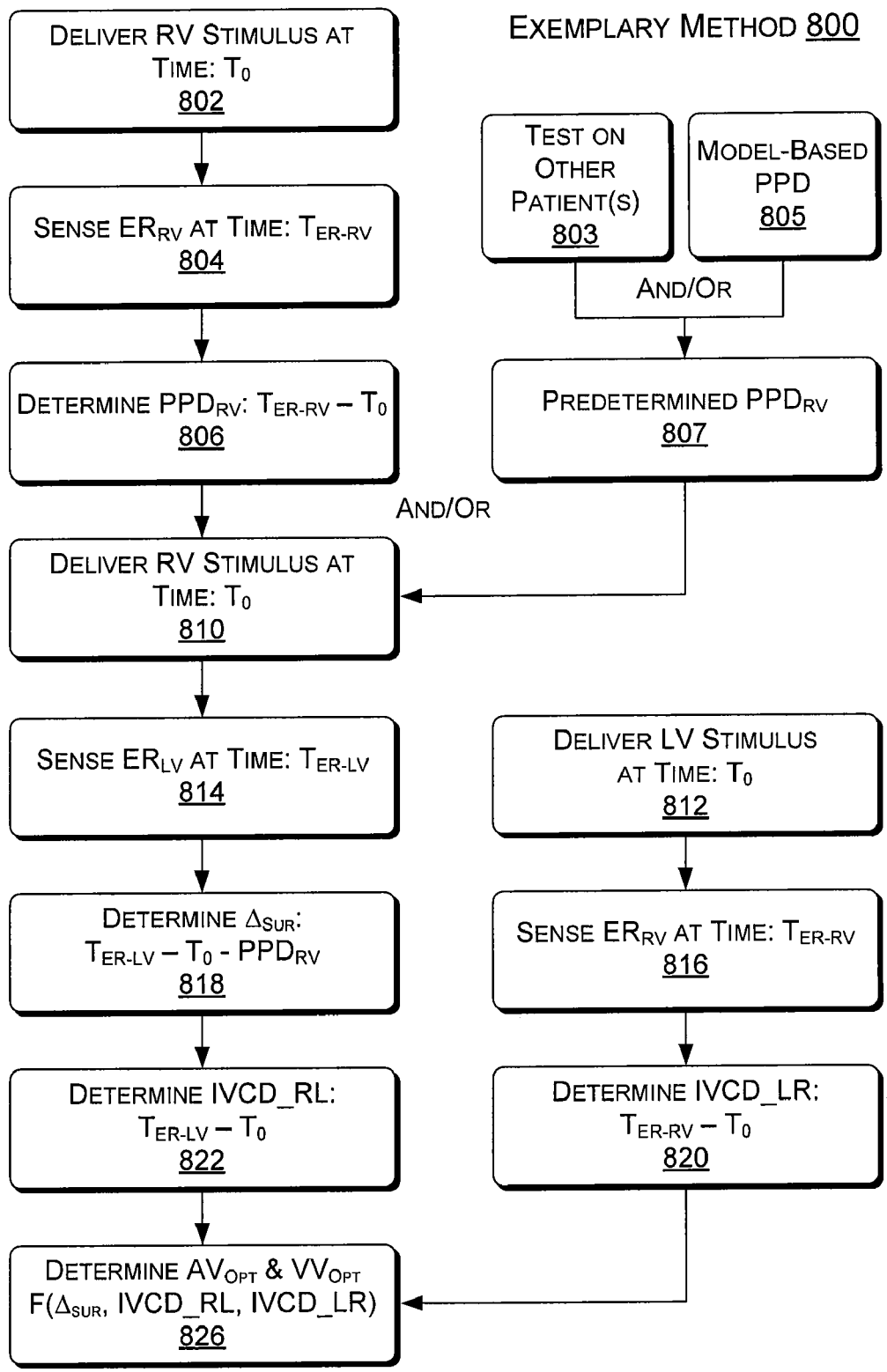
FIG. 8 is a block diagram of an exemplary method for determining one or more parameters for delivery of a pacing therapy based at least in part on a ventricular paced propagation delay.

FIG. 8 shows an exemplary method 800 that uses the technique 720 to aid in determination of one or more pacing parameters (e.g., using the optimization method of FIG. 4). The method 800 commences in a delivery block 802 that delivers a stimulus to the RV at a time $T_0$. A sense block 804 follows that senses an evoked response ($ER_{RV}$) at a time $T_{ER-RV}$. A determination block 806 determines a paced propagation delay for the RV ($PPD_{RV}$) as the difference between $T_{ER-RV}$ and $T_0$.

FIG. 8 also shows alternative manners to determine a value for $PPD_{RV}$. For example, a test block 803 performs tests or accesses test results performed on other patients and then uses such information to arrive at a $PPD_{RV}$ value, which, per block 807, is considered a predetermined value for purposes of the method 800. In another example, a model 805 is used to provide a predetermined value per block 807. As indicated a combination of techniques may be used to arrive at a suitable $PPD_{RV}$ value.

According to the method 800, once a value is provided for $PPD_{RV}$, a surrogate value for $\Delta$ (e.g., $\Delta_{Sur}$) may be determined on an as needed basis. For example, provided a $PPD_{RV}$, the method 800 continues in a delivery block 810 that delivers a RV stimulus at a time $T_0$. Next, a sense block 814 senses an evoked response ($ER_{LV}$) in the other ventricle at a time $T_{ER-LV}$, where the evoked response is caused by the RV stimulus. A determination block 818 follows that determines a surrogate value for $\Delta$ (e.g., $\Delta_{Sur}$) as $T_{ER-LV}-T_0-PPD_{RV}$. Inherent in this approach is the fact that information for determination of IVCD_RL is already provided, hence, a determination block 822 determines IVCD_RL as $T_{ER-LV}-T_0$. In general, IVCD_RL and IVCD_LR rely on time of delivery of the stimulus (e.g., $T_0$) such that paced propagation delay can be considered as "built-in" to the directional interventricular conduction time. However, as mentioned, other possibilities exist for determination of IVCD_RL or IVCD_LR.

The method 800 also includes delivery of an LV stimulus at a time $T_0$ per delivery block 812, sensing an evoked response in the RV ($ER_{RV}$) at a time $T_{ER-RV}$ per sense block 816 and determination of IVCD_LR as $T_{ER-RV}-T_0$ per determination block 820. Given the appropriate values (e.g., $\Delta_{Sur}$, IVCD_RL and IVCD_LR), a determination block 826 determines one or more pacing parameters such as $AV_{Opt}$ and $VV_{Opt}$.

FIG. 9 shows an exemplary scenario 900 where an atrial arrhythmia exists. As explained with respect to FIG. 9, an atrial arrhythmia can confound measurement of IVCD_RL and IVCD_LR. In the scenario 910 an atrial arrhythmia exists as indicated by a string of atrial events 911 (e.g., coarse atrial fibrillation). Depending on characteristics of atrio-ventricular node conduction (e.g., 2:1 block, total block, etc.), in general, some of the atrial events 911 will conduct to the left ventricle and generate R waves ($R_{LV}$), as indicated by the R wave 915. According to the scenario 910, the intrinsic R wave 915 occurs before conduction from the RV stimulus conducts to the left ventricular sensing location 916. Thus, measurement of IVCD_RL may be problematic.

As described herein, various techniques provide for measurement of IVCD_RL or IVCD_LR where (ii) abnormal atrial activity such as atrial fibrillation exists. For example, FIG. 9 shows an exemplary method 920 that uses discrimination for IVCD sensing where abnormal atrial activity exists. The method 920 commences in a detection block 922 that detects an atrial arrhythmia. In response, an implementation block 926 implements discrimination for IVCD sensing. As indicated by block 924, discrimination may rely on a sensing window, a template and/or waveform analysis.

With respect to a sensing window, consider sensing right ventricular activity. An atrial event occurs and according to $PV_{LV}$, a stimulus is delivered to the left ventricle that generates an evoked response. Before the wavefront from the left ventricular stimulus conducts to the right ventricle, the atrial event conducts to the right ventricle and generates an R wave. However, a sensing window, for purposes of measuring IVCD_LR, does not commence until after $PR_{RV}$.

With respect to use of a template, one or more right ventricular IEGMs may be analyzed and used to discriminate right ventricular activity caused by atrial activity from right ventricular activity caused by delivery of a stimulus to the left ventricle. As to waveform analysis, one or more right ventricular IEGMs may be analyzed to identify a characteristic or characteristics that can be used to discriminate right ventricular activity caused by atrial activity from right ventricular activity caused by delivery of a stimulus to the left ventricle.

Per the method 920, measurement of IVCD_RL and/or IVCD_LR occurs using discrimination, for example, to ensure that an event such as the event 915 does not confound measurement of a IVCD_RL value or a IVCD_LR value. Next, a determination block 934 determines a value for $\Delta_{Sur}$ using IVCD_RL and $PPD_{RV}$ (e.g., $\Delta_{Sur}$=IVCD_RL$-PL_{RV}$).

FIG. 10 shows exemplary techniques 1000, which rely on measurement of one or more intervals to determine a surrogate value $\Delta_{Sur}$ for the parameter $\Delta$. The examples in FIG. 10 pertain to situations where RV activity occurs prior to LV activity (i.e., "RV first"). A plot 1010 shows RV activity and LV activity along contemporaneous time lines (e.g., sensing channels) for three cardiac cycles, labeled C1, C2 and C3 where the RV contracts prior to the LV ("RV first"). In the plot 1010, the RV activity and the LV activity is assumed to be based on conduction of atrial activity. As mentioned, RV activity and the LV activity can be present during atrial arrhythmia where, depending on the nature of the atrial arrhythmia, the AVN may slow conduction or block conduction to some degree. However, RV activity and LV activity during an episode of atrial arrhythmia may conduct to one or both ventricles and hence confound measurement of PR, AR, a $R_{RV}$ to $R_{LV}$ interval or an $R_{LV}$ to $R_{RV}$ interval. As described herein, one or more interval values measured during a normal rhythmic period can be used to determine a surrogate value $\Delta_{Sur}$ for the parameter $\Delta$.

The intervals shown in the plot 1010 include a $R_{RV}-R_{RV}$ interval, a $R_{RV}-R_{LV}$ interval, a $R_{LV}-R_{LV}$ interval and a $R_{LV}-R_{RV}$ interval. Exemplary methods 1020, 1030 and 1040 include use of one or more of these intervals to determine a surrogate value $\Delta_{Sur}$ for the parameter $\Delta$. Once determined, the method 1020, 1030 or 1040 may use the value to optimize one or more pacing parameters (e.g., AV, PV and/or W), for example, as described with respect to the method 400 of FIG. 4.

The method 1020 includes an acquisition block 1022 that acquires a value for the interval $R_{RV}-R_{LV}$. Per a determination block 1026, this value may be used directly as a surrogate for $\Delta$, (i.e., $\Delta_{Sur}$) which would otherwise be determined based on PR and/or AR measurements. Depending on convention, the value may require multiplication by "−1" (e.g., where $\Delta=PR_{IN}-PR_{RV}$). An optimization block 1028 then optimizes one or more pacing parameters based at least in part on the $\Delta_{Sur}$ value. If the LV activity occurred prior to the RV activity (i.e., "LV first"), then the interval would be $R_{LV}-R_{RV}$.

The method 1030 includes an acquisition block 1032 that acquires a value for the interval $R_{RV}-R_{RV}$ and an acquisition block 1034 that acquires a value for the interval $R_{LV}-R_{RV}$. Per a determination block 1036, these values may be used to determine a surrogate for $\Delta$, (i.e., $\Delta_{Sur}$) which would otherwise be determined based on PR and/or AR measurements. Specifically, the value for $\Delta_{Sur}$ can be calculated as the difference $R_{RV}-R_{RV}-R_{LV}-R_{RV}$. Depending on convention, the value may require multiplication by "−1" (e.g., where $\Delta=PR_{LV}-PR_{RV}$). An optimization block 1038 then optimizes one or more pacing parameters based at least in part on the $\Delta_{Sur}$ value. If the LV activity occurred prior to the RV activity (i.e., "LV first"), then the difference could be calculated as $R_{LV}-R_{LV}-R_{RV}-R_{LV}$ (with respective changes for acquisition blocks 1032 and 1034).

The method 1040 includes an acquisition block 1042 that acquires a value for the interval $R_{LV}-R_{LV}$ and an acquisition block 1044 that acquires a value for the interval $R_{LV}-R_{RV}$. Per a determination block 1046, these values may be used to determine a surrogate for $\Delta$, (i.e., $\Delta_{Sur}$) which would otherwise be determined based on PR and/or AR measurements. Specifically, the value for $\Delta_{Sur}$ can be calculated as the difference $R_{LV}$–$R_{LV}$–$R_{LV}$–$R_{RV}$. Depending on convention, the value may require multiplication by "–1" (e.g., where $\Delta$=$PR_{IN}$–$PR_{RV}$). An optimization block 1048 then optimizes one or more pacing parameters based at least in part on the $\Delta_{Sur}$ value. If the LV activity occurred prior to the RV activity (i.e., "LV first"), then the difference could be calculated as $R_{RV}$–$R_{RV}$–$R_{RV}$–$R_{LV}$ (with respective changes for acquisition blocks 1042 and 1044).

Figure 11:
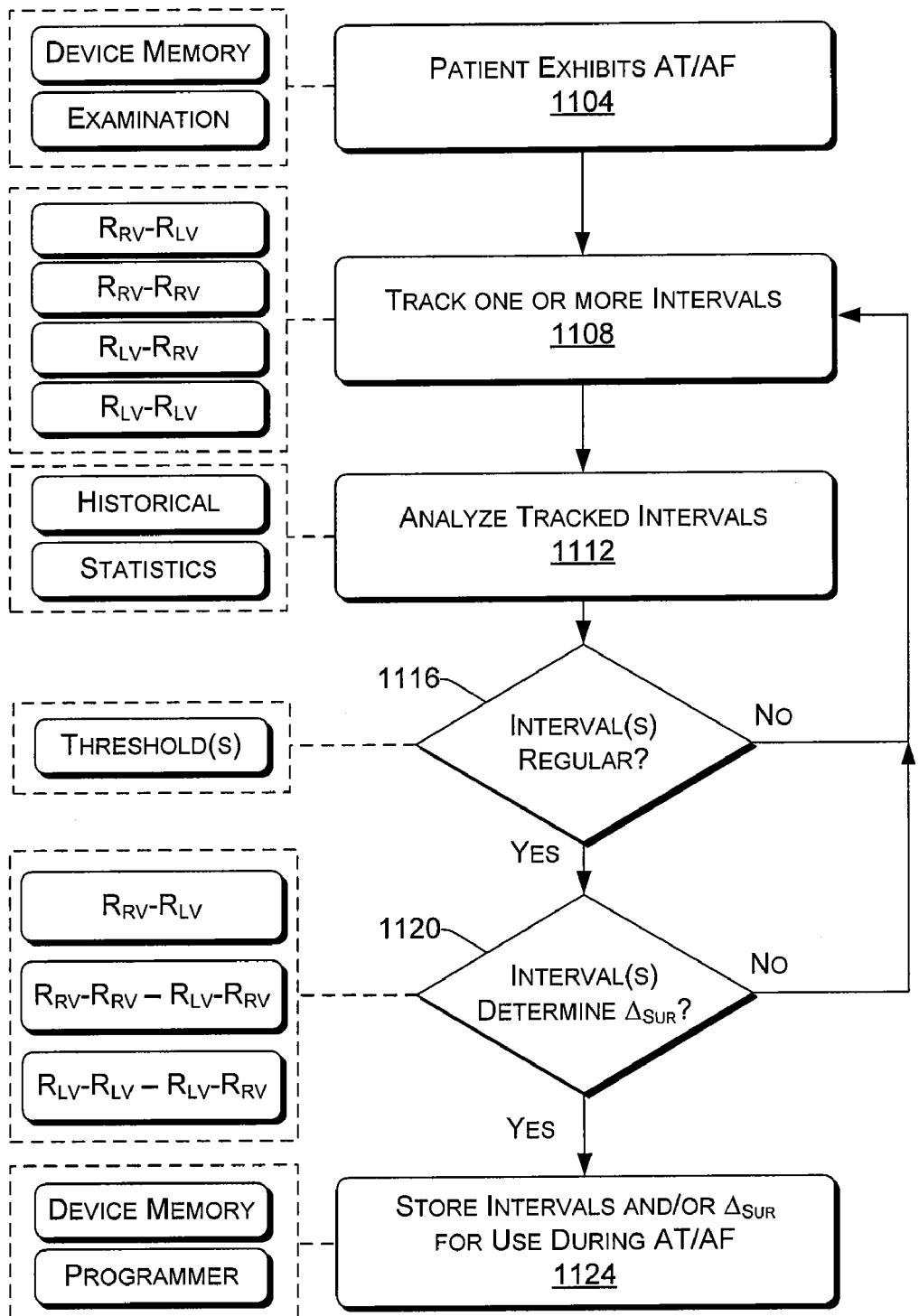
FIG. 11 is a block diagram of an exemplary method for acquiring interval information and deciding whether such information is suitable for use in determining the parameter $\Delta$.

FIG. 11 shows an exemplary method 1100 for determining a surrogate value for $\Delta$ (i.e., $\Delta_{Sur}$) based at least in part on one or more intervals. The method 1100 commences in a diagnosis block 1104 where a clinician or an implantable device notes that a patient suffers from episodes of AT and/or AF. The diagnosis may be the result of a clinical exam and/or information stored in memory of an implantable device. In the latter case, the implantable device may automatically respond to the diagnosis (e.g., evidence of AT/AF) by initiating interval tracking and analysis.

In the method 1100, a clinician instructs the device to commence interval tracking, for example, per a tracking block 1108 that tracks one or more intervals. After or during acquisition of interval information (e.g., tracking), an analysis block 1112 analyzes the information, for example, using historical information and/or statistical techniques. The analysis block 1112 aims to provide one or more metrics as to the consistency of the intervals.

As shown in FIG. 11, the method 1100 includes a decision block 1116 that decides whether the analyzed interval or intervals are sufficiently regular. For example, the decision block 1116 may compare an interval average to a threshold or an interval standard deviation to a threshold. If the decision block 1116 decides that the intervals are not sufficiently regular, then the method 1100 continues at the tracking block 1108; otherwise, the method 1100 continues at another decision block 1120.

The decision block 1120 decides whether the sufficiently regular intervals can be used to determine a surrogate value for $\Delta$ (i.e., $\Delta_{Sur}$). For example, if $R_{RV}$–$R_{LV}$ (for $R_{RV}$ occurring before $R_{LV}$) is regular, then this interval may be used to determine a surrogate value. While not shown, if $R_{LV}$ occurs prior to $R_{RV}$ and the interval $R_{LV}$–$R_{RV}$ is regular, then this interval may be used to determine a surrogate value. Other interval decisions rely on $R_{RV}$–$R_{RV}$ or $R_{LV}$–$R_{LV}$ being regular. If the decision block 1120 decides that one or more intervals are available to determine a surrogate value, then the method 1100 proceeds to block 1124, which stores one or more regular intervals, as appropriate, for determination of $\Delta_{Sur}$ and/or it stores one or more calculated $\Delta_{Sur}$ values. Also, if a patient has some intrinsic atrio-ventricular conduction, then appropriate AR or PR intervals may be stored and used alternatively or in conjunction with any of the tracked intervals (e.g., during AT/AF).

With respect to interval regularity, an exemplary method may rely on a criterion or criteria such as, given eight consecutive cardiac cycles (C1-C8), does the interval vary by less than +/–10% of the average. Such an example may use a standard deviation and compare it to a standard deviation criterion.

The method 1100 may be used in instances where (i) atrial conduction exists yet (ii) atrial tracking is disabled, either temporarily and/or permanently. For example, a convention algorithm implemented by an implantable pacing device includes atrial tracking to track atrial events, however, if the rate of atrial events exceeds a limit, the algorithm calls for turning off atrial tracking. Given such a scenario, PR cannot be readily measured and hence the interval method 1100 of FIG. 11 may be implemented. Where an implantable device acquires and stores interval information, such information may be recalled from memory and used to determine a surrogate value $\Delta_{Sur}$.

An exemplary method may periodically disable ventricular pacing to acquire interval information and then re-enable ventricular pacing after acquisition of the interval information. Such a method may disable ventricular pacing during the night or at other times when non-pacing poses little risk. For example, during the night an exemplary method may disable pacing for a couple of cardiac cycles to acquire AR and/or PR interval information.

According to various exemplary methods, devices, systems, etc., information acquired (e.g., pacing latencies, intervals, $\Delta$, $\Delta_{Sur}$, pacing parameters, etc.) may be used to diagnose cardiac condition. For example, an exemplary method may track AV delays and/or VV delays over time where the delays are determined at least in part on pacing latency and/or interval information. Such information may then be used to determine subsequent therapy.

Various exemplary methods, devices, systems, etc., include determining an optimal interventricular delay (e.g., $\Delta_{Opt}$), an optimal AV (e.g., $AV_{Opt}$) and/or an optimal VV (e.g., $VV_{Opt}$) using a modality such as an echocardiogram. Any of a variety of internal sensors (e.g., implantable hemodynamic sensors) may be available or become available and be able to measure such optimal delays for a variety of patient circumstances (e.g., sleep, exercise, etc.). Accordingly, an exemplary method, device, system, etc., includes use of one or more internal sensors to measure and/or update such an optimal delay and/or to determine values for one or more parameters related to an optimal delay. For example, a blood pressure sensor (e.g., aortic arch, left atrium, etc.) may be used to determine or to update an optimal delay. Further, information may be collected over a period of time to determine heart condition (e.g., deterioration, improvement, etc.).

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

As described herein, various techniques include adjusting one or more pacing parameters based at least in part on patient activity. Such techniques may use variables such as $\Delta P$, $\Delta A$, DD and/or AD where $\Delta P$ and $\Delta A$ are width of atrial activity and DD and AD are intervals measured, for example, from the end of an atrial wave to an R wave or suitable detection point on an R wave (e.g., peak, slope, etc.). Two parameters, $\delta$ and $\beta$, are discussed in more detail below. The parameter $\delta$ may depend on $\Delta P$ or $\Delta A$ while the parameter $\beta$ may depend on $\delta$ and DD or AD, as indicated by the following equations:

$$\delta = f(\Delta P) \text{ or } f(\Delta A)$$

$$\beta = \delta/DD \text{ or } \delta/AD$$

These parameters may be used to determine one or more pacing parameters, for example, as indicated by the following equations:

$$PV = \Delta P + \beta * DD$$

$$AV = \Delta A + \beta * AD$$

(for some variations of these four equations see FIG. 12). The PV or AV forms may be used to determine an optimal PV or AV. For example, $AV_{opt}$ may be determined and then used in any of the various scenarios of FIG. 5. For VV delay, techniques described above may be used. However, as discussed in more detail below, VV may depend on activity and hence may change when activity state changes. VV is used for bi-ventricular pacing and the following equations may be used:

$$PV'' = PV' + VV$$

$$AV'' = AV' + VV$$

where PV' and AV' are for the master ventricle and where PV''' and AV''' are for the slave ventricle.

Various exemplary method discussed herein include sensing patient activity, for example, using an activity sensor (e.g., accelerometer, minute ventilation, etc.), and adjusting one or more pacing parameters based at least in part on such sensing. An exemplary method may select a pacing parameter for a pacing therapy based on patient activity state. For example, an implantable device may include a set of parameters for a rest state and a set of parameters for an exercise state.

An exemplary method may include monitoring one or more characteristics of atrial activity and adjusting one or more pacing parameters based at least in part on such monitoring. For example, a method may include monitoring P wave width (e.g., $\Delta P$) and using P wave width to adjust one or more pacing parameters whereas another method may include monitoring A wave width (e.g., $\Delta A$) and using A wave width to adjust one or more pacing parameters. P wave width or A wave width may increase as patient activity increases. Thus, if the P wave width or the A wave width exceed a limit, then an exemplary method may call for a change in one or more pacing parameters.

An exemplary method may include disabling ventricular pacing and measuring DD interval or AD interval, respectively, and adjusting one or more pacing parameters based at least in part on such measuring. DD interval or AD interval may increase as patient activity increases. Thus, if the DD interval (e.g., $DD_{RV}$ or $DD_{LV}$) or the AD interval (e.g., $AD_{RV}$ or $AD_{LV}$) exceed a limit, then an exemplary method may call for a change in one or more pacing parameters.

An exemplary method may include sensing PP interval as a surrogate for patient activity and adjusting one or more pacing parameters based at least in part on such sensing. In general, PP interval will decrease as patient activity increases; noting that certain conditions or drugs may make this technique less useful (e.g., beta blockers, high NYHA class, etc.). While PP interval is mentioned, other intervals may be used based on a marker that occurs once per cardiac cycle (e.g., $R_{RV}$, $R_{LV}$, etc.). An exemplary method may select a pacing parameter for a pacing therapy based on an interval. For example, an implantable device may include a set of parameters for a long interval (e.g., a rest state) and a set of parameters for a short interval (e.g., an exercise state).

While the foregoing discussion pertains to schemes individually, an exemplary method may use any of the various schemes, as appropriate. For example, an exemplary method may include monitoring P wave width and disabling ventricular pacing to measure DD interval based at least in part on P wave width.

FIG. 12 shows various exemplary methods 1200. While equations are presented, implementation of techniques described herein may be implemented using any of a variety of forms of control logic. For example, look-up tables may be used together with logic that stores and/or pulls data from the look-up table. Control logic to achieve the overall goals achieved by the various equations 1200 may be achieved by control logic that does not explicitly rely on the equations, as presented. In instances where the parameter $\Delta$ appears, various exemplary method described herein can be used, as appropriate, to determine one or more surrogate values $\Delta_{Sur}$.

A state block 1210 defines various activity states. The activity states include a base state, for example, a rest state denoted by a subscript "0". In other examples, the subscript "rest" is used. The activity states include at least two states, for example, a base state and another activity state. In FIG. 12, the states range from the base state to activity state "N", which may be an integer without any numeric limitation (e.g., N may equal 5, 10, 100, 1000, etc.). The number of activity states may depend on patient condition and patient activity. For example, a patient that is bedridden may have few activity states when compared to a young patient (e.g., 40 years old) fitted with a pacemaker that leads an active life with a regular exercise regimen.

A PV or AV states block 1220 presents equations for the parameters $\beta$ and $\delta$ as well as for a base state PV and AV and PV and AV for a state other than a base activity state, referred to as $AS_x$, where x=1, 2, ... N. In addition, sets of equations are presented that include a pacing latency term PL. Pacing latency is generally defined as the time between delivery of a cardiac stimulus and time of an evoked response caused by the stimulus. More specifically, an implantable device may use the time of delivery of a stimulus and the time at which a sensed, evoked response signal deviates from a baseline, which is referred to herein as $PL_I$ (e.g., to initiation of evoked response). Such a signal is usually sensed using the lead that delivered the stimulus, however, electrode configuration may differ (e.g., unipolar delivery and bipolar sensing, bipolar delivery and unipolar sensing, etc.). In some instances, the pacing latency may exceed 100 ms due to ischemia, scarring, infarct, etc. Thus, PV or AV timing may be adjusted accordingly to call for earlier delivery of a stimulus to a ventricle or ventricles.

An exemplary algorithm may determine PL for the right ventricle (for a right ventricular lead) and for the left ventricle (for a left ventricular lead) during measurement of IVCD-LR and IVCD-RL (e.g., parameters that may be used to determine VV). While pacing latency can be measured from the time of delivering a pacing pulse to the time of an evoked response at the pacing lead ($PL_I$), pacing latency may be measured alternatively from the time of the pulse to the peak of an evoked response ($PL_{Peak}$). In either instance, such techniques may shorten block and/or discharge periods, optionally to a minimum (e.g., about 3 ms in some commercial ICDs). An algorithm may also provide for detection of capture, for example, using an integral (e.g., PDI) and/or a derivative (e.g., $D_{max}$). In general, pacing latencies for LV and RV leads correspond to situations where capture occurs. In yet another alternative, during P wave and PR measurement, a time delay from a marker of a sensed R event to the peak of a QRS complex may be measured and used as a correction term akin to pacing latency.

A VV states block 1230 presents equations for the parameters $\alpha$, $\Delta$ and $\Delta_{IVCD}$ and VV for a base activity state ($AS_0$) and another activity state ($AS_x$). These equations may be used in various scenarios of the methods presented herein (see, e.g., exemplary methods 400, 500, 800, 1000 and 1100). Noting that some differences exist between the method 500 and the equations of FIG. 12, for example, lack of absolute values for the parameter $\Delta$. To account for this variation, the value of $\Delta$ is used to determine whether the right ventricle or left ventricle is paced for single ventricle pacing or is the master for bi-ventricular pacing. If the $\Delta$ is less than 0 ms, then the right ventricle is paced or the master whereas if $\Delta$ is greater than 0 ms, then the left ventricle is paced or the master. For bi-ventricular pacing, the PV or AV state equation is used for the master ventricle and then the VV equation is used to determine timing of the slave ventricle. Hence, the control logic uses $\Delta$ to determine whether the PV or AV state equation will correspond to the left ventricle or the right ventricle. As described herein, one or more pacing latencies and/or one or more intervals may be used to determine the parameter $\Delta$ (e.g., $\Delta_{Sur}$), for example, where straightforward measurement of PR and/or AR for the RV and/or LV is not possible or problematic (e.g., due to atrial fibrillation).

The block 1230 also includes equations for a pacing latency differential, referred to as $\Delta PL$. This term may be calculated, for example, as the difference between $PL_{Peak}$ and a generic or average pacing latency (e.g., $PL_{Ave}$ based on a sampling of "normal" pacing latencies). Hence, $\Delta PL$ may represent a difference from a normal pacing latency. A normal pacing latency may be around 70 ms and hence $\Delta PL$ may equal $PL_{Peak}$ minus 70 ms. The parameter $\Delta PL$ may be calculated for both the right ventricle (e.g., $\Delta PL$–RV) and the left ventricle (e.g., $\Delta PL$–LV). Where VV has positive sign that indicates to pace LV first, then the correction term $\Delta PL$–LV may be added while where VV has a negative sign that indicates to pace RV first then the correction term $\Delta PL$–RV may be added. In block 1230, the term $\Delta PL$ is shown without indication of LV or RV, noting that use of $\Delta PL$–LV or $\Delta PL$–RV may be determined accordingly. A criterion or criteria may be used to decide if a pacing latency correction term should be used in determining PV, AV or VV. For example, if PL exceeds a certain limit, then a pacing latency correction term or terms may be used. Similarly, if $\Delta PL$ exceeds a certain limit, then a pacing latency correction term or terms may be used.

Recent clinical data indicates that during exercise, optimal PV/AV delays are prolonged compared with those at rest in HF patients. Various exemplary techniques described herein can account for changes for HF patients during exercise and at rest through the duration of P wave or A wave and an appropriate atrio-ventricular conduction delay. During exercise some HF patients may have an increase in width of atrial signals or atrio-ventricular conduction delays or both that would lead to prolonged optimal AV and PV delays. In patients with normal rate responses, AV or PV delays may have negative hysteresis or remain the same as at rest.

While various examples mention use of a "rest" state, a rest state may be a base state. Alternatively, a base state may be a state other than a rest state. For example, a base state may correspond to a low activity state where a patient performs certain low energy movements (e.g., slow walking, swaying, etc.) that may be encountered regularly throughout a patient's day. Thus, a base state may be selected as a commonly encountered state in a patient's waking day, which may act to minimize adjustments to PV, AV or VV. Further, upon entering a sleep state, a device may turn off adjustments to PV, AV or VV and assume sleep state values for PV, AV or W. Such decisions may be made according to a timer, a schedule, an activity sensor, etc.

An exemplary computing device may include control logic to assess cardiac condition based at least in part on information acquired from an implantable device where the information includes, for example, one or more CRT parameter and/or one or more rate adaptive pacing parameters or combinations thereof (e.g., $\alpha$, $\Delta$, IVCD-RL, IVCD-LR, $\Delta_{IVCD}$), AV, PV, VV, response time, recovery time, $Th_{ID}$, $Th_{AD}$, $Slope_{R/A}$, etc.). The computing device may be the implantable device, or in other words, an implantable device may be capable of assessing patient condition and more particularly cardiac condition.

Various exemplary methods may be implementable wholly or to varying extent using one or more computer-readable media that include processor executable instructions for performing one or more actions. For example, the device 100 of FIG. 2 shows various modules associated with a processor 220. Hence, a module may be developed using an algorithm described herein. Such a module may be downloadable to an implantable device using a device programmer or may be incorporated into a device during manufacture by any of a variety of techniques. At times such instructions are referred to as control logic.

Figure 13:
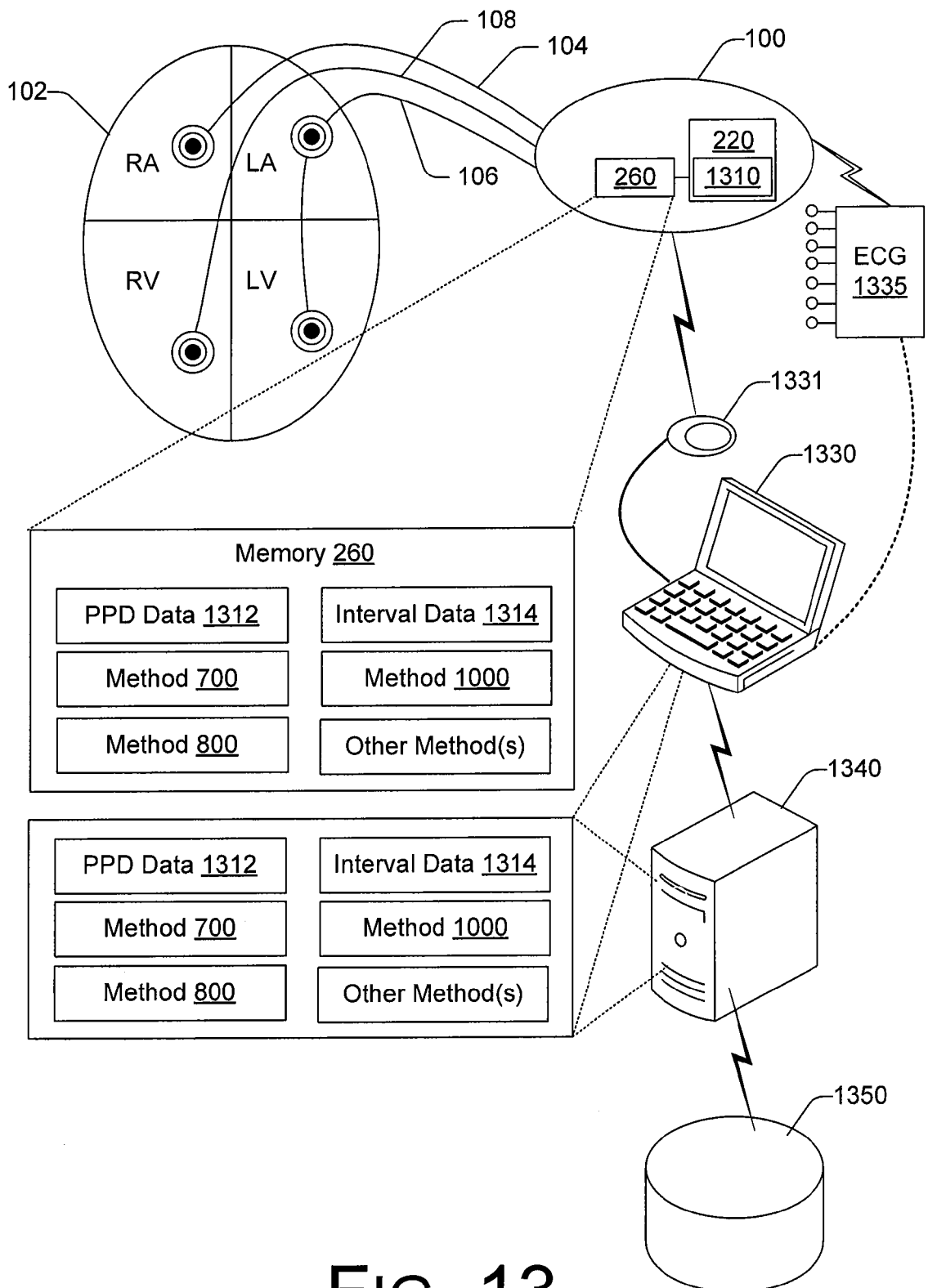
FIG. 13 is a diagram of an exemplary system capable of implementing various exemplary methods.

FIG. 13 shows an exemplary system 1300 that includes the exemplary implantable device 100 of FIGS. 1 and 2, with processor 220 including one or more modules 1310, for example, that may be loaded via memory 260. A series of leads 104, 106 and 108 provide for delivery of stimulation energy and/or sensing of cardiac activity, etc., associated with the heart 102. Stylized bullets indicate approximate positions or functionality associated with each of the leads 104, 106 and 108. Other arrangements are possible as well as use of other types of sensors, electrodes, etc.

Memory 260 is shown as including PPD data 1312, interval data 1314 where such data may include one or more measures, pacing parameters, historical interval values, etc. Memory 260 also includes appropriate modules (e.g., processor-executable instructions) for performing various actions of the methods 700, 800, 1000, etc., noting that part of a method may be performed using a device other than the implantable device 100. For example, for acquisition of ECG information, an ECG unit 1335 may be used, which optionally communicates with the device 100 or one or more other devices (e.g., the device 1330, 1340, etc.)

The system 1300 includes a device programmer 1330 having a wand unit 1331 for communicating with the implantable device 100. The programmer 1330 may further include communication circuitry for communication with another computing device 1340, which may be a server. The computing device 1340 may be configured to access one or more data stores 1350, for example, such as a database of information germane to a patient, an implantable device, therapies, etc.

The programmer 1330 and/or the computing device 1340 may include various information such as the PPD data 1312, the interval data 1314 and modules (e.g., processor-executable instructions) for performing various actions of the methods 700, 800, 1000, etc., noting that a particular implementation of a method use more than one device.

The programmer 1330 optionally includes features of the commercially available model number 3510 programmer and/or the MERLIN™ programmer marketed by St. Jude Medical, Sylmar, Calif. The MERLIN™ programmer includes a processor, ECC (error-correction code) memory, a touch screen, an internal printer, I/O interfaces such as a USB that allows a device to connect to the internal printer and attachment of external peripherals such as flash drives, Ethernet, modem and WiFi network interfaces connected through a PCMCIA/CardBus interface, and interfaces to ECG and RF (radio frequency) telemetry equipment. The programmer 1330 may be capable of displaying one or more GUIs, for example, to enable a method, program the device 100, assess PPD data 1312 and/or interval data 1314, etc.

The wand unit 1331 optionally includes features of commercially available wands. As shown, the wand unit 1331 attaches to a programmer 1330, which enables clinicians to conduct implantation testing and performance threshold testing, as well as programming and interrogation of pacemakers, implantable cardioverter defibrillators (ICDs), emerging indications devices, etc.

During implant, a system such as a pacing system analyzer (PSA) may be used to acquire information, for example, via one or more leads. A commercially available device marketed as WANDA™ (St. Jude Medical, Sylmar, Calif.) may be used in conjunction with a programmer such as the MERLIN™ programmer or other computing device (e.g., a device that includes a processor to operate according to firmware, software, etc.). Various exemplary techniques described herein may be implemented during implantation and/or after implantation of a device configured for delivery of electrical stimulation (e.g., leads and/or pulse generator) and the types of equipment for acquiring and/or analyzing information may be selected accordingly.

The wand unit 1331 and the programmer 1330 allow for display of atrial and ventricular electrograms simultaneously during a testing procedure. Relevant test measurements, along with customizable implant data, can be displayed, stored, and/or printed in a comprehensive summary report for the patient's medical records and physician review and/or for other purposes.

In the example of FIG. 13, the data store 1350 may include information such as measures (e.g., ventricular PLs or intervals), values, scores, etc. Such information may be used by a model, in making a comparison, in making a decision, in adjusting a therapy, etc. Such information may be updated periodically, for example, as the device 100 (or other device(s)) acquires new patient information. The system 1300 is an example as other equipment, instructions, etc., may be used or substituted for features shown in FIG. 13.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
 delivering a cardiac pacing therapy that comprises an atrio-ventricular delay (AV or PV) and an interventricular delay (VV);
 disabling ventricular pacing;
 acquire $R_{RV}$ and $R_{LV}$;
 if $R_{RV}$ occurs prior to $R_{LV}$ in a cardiac cycle then
  acquiring a $R_{RV}-R_{RV}$ interval,
  acquiring a $R_{LV}-R_{RV}$ interval, and
  determining an interventricular delay ($\Delta_{Sur}$) based on the acquired $R_{RV}-R_{RV}$ interval and $R_{LV}-R_{RV}$ interval; or
 if $R_{LV}$ occurs prior to $R_{RV}$ in a cardiac cycle then
  acquiring a $R_{LV}-R_{LV}$ interval,
  acquiring a $R_{RV}-R_{LV}$ interval, and
  determining an interventricular delay ($\Delta_{Sur}$) based on the acquired $R_{LV}-R_{LV}$ interval and $R_{RV}-R_{LV}$ interval; and
 determine one or more cardiac pacing therapy parameters based at least in part on the intraventricular delay ($\Delta_{Sur}$) in order to optimize pacing therapy based on the determined one or more cardiac pacing therapy parameters.

2. The method of claim 1 further comprising enabling ventricular pacing according to at least one of the determined parameters.

3. The method of claim 2 wherein the enabling occurs responsive to detection of an atrial arrhythmia.

4. The method of claim 2 wherein the enabling occurs responsive to detection of a conduction block.

5. The method of claim 4 wherein the conduction block comprises an atrio-ventricular nodal block.

6. The method of claim 1 wherein the one or more cardiac pacing therapy parameters comprises an interventricular pacing delay (VV) or an atrio-ventricular pacing delay (AV or PV).

7. The method of claim 1 further comprising enabling ventricular pacing according to the determined atrio-ventricular delay wherein pacing of the right ventricle occurs prior to pacing of the left ventricle by the determined interventricular delay ($\Delta_{Sur}$).

8. The method of claim 1 further comprising enabling ventricular pacing according to the determined atrio-ventricular delay wherein pacing of the left ventricle occurs prior to pacing of the right ventricle by the determined interventricular delay ($\Delta_{Sur}$).

9. A method comprising:
 delivering a cardiac pacing therapy that comprises an atrio-ventricular delay (AV or PV) and an interventricular delay (VV);
 disabling ventricular pacing;
 acquire $R_{RV}$ and $R_{LV}$;
 if $R_{RV}$ occurs prior to $R_{LV}$ in a cardiac cycle then
  acquiring a $R_{LV}-R_{LV}$ interval,
  acquiring a $R_{LV}-R_{RV}$ interval, and
  determining an interventricular delay ($\Delta_{Sur}$) based on the acquired $R_{LV}-R_{LV}$ interval and $R_{LV}-R_{RV}$ interval; or
 if $R_{LV}$ occurs prior to $R_{RV}$ in a cardiac cycle then
  acquiring a $R_{RV}-R_{RV}$ interval,
  acquiring a $R_{RV}-R_{LV}$ interval, and
  determining an interventricular delay ($\Delta_{Sur}$) based on the acquired $R_{RV}-R_{RV}$ interval and $R_{RV}-R_{LV}$ interval; and
 determine one or more cardiac pacing therapy parameters based at least in part on the intraventricular delay ($\Delta_{Sur}$) in order to optimize pacing therapy based on the determined one or more cardiac pacing therapy parameters.

10. The method of claim 9 further comprising enabling ventricular pacing according to at least one of the determined parameters.

11. The method of claim 9 wherein the one or more cardiac pacing therapy parameters comprises an interventricular pacing delay (VV) or an atrio-ventricular pacing delay (AV or PV).

* * * * *